US 9,491,941 B2

(12) United States Patent
Dupont et al.

(10) Patent No.: US 9,491,941 B2
(45) Date of Patent: Nov. 15, 2016

(54) (HETERO) ARYLACRYLAMIDES FOR THE CONTROL OF ECTOPARASITES

(71) Applicant: Novartis Tiergesundheit AG, Basel (CH)

(72) Inventors: Emilie Dupont, Saint Louis (FR); Noelle Gauvry, Kembs (FR); Steve Nanchen, Basel (CH); Chikako Ogawa, Basel (CH); Chouaib Tahtaoui, Rixheim (FR)

(73) Assignee: NOVARTIS TIERGESUNDHEIT AG, Basel (CH)

( * ) Notice: Subject to any disclaimer, the term of this patent is extended or adjusted under 35 U.S.C. 154(b) by 0 days.

(21) Appl. No.: 14/649,268

(22) PCT Filed: Dec. 20, 2013

(86) PCT No.: PCT/EP2013/077739
§ 371 (c)(1),
(2) Date: Jun. 3, 2015

(87) PCT Pub. No.: WO2014/096381
PCT Pub. Date: Jun. 26, 2014

(65) Prior Publication Data
US 2015/0320044 A1    Nov. 12, 2015

(30) Foreign Application Priority Data

Dec. 20, 2012   (EP) ...................................... 12198758
Dec. 9, 2013    (CH) ........................................ 2036/13

(51) Int. Cl.
*C07C 233/66* (2006.01)
*C07C 255/48* (2006.01)
*A01N 37/34* (2006.01)
*A01N 37/18* (2006.01)
*C07D 305/06* (2006.01)
*A01N 37/30* (2006.01)
*A01N 43/08* (2006.01)
(Continued)

(52) U.S. Cl.
CPC ............... *A01N 37/34* (2013.01); *A01N 37/18* (2013.01); *A01N 37/30* (2013.01); *A01N 43/08* (2013.01); *A01N 43/10* (2013.01); *A01N 43/16* (2013.01); *A01N 43/20* (2013.01); *A01N 43/36* (2013.01); *A01N 43/40* (2013.01); *A01N 43/42* (2013.01); *A01N 43/44* (2013.01); *A01N 43/80* (2013.01); *A01N 47/16* (2013.01); *C07C 233/65* (2013.01); *C07C 233/66* (2013.01); *C07C 233/69* (2013.01); *C07C 237/22* (2013.01); *C07C 255/29* (2013.01); *C07C 255/46* (2013.01); *C07C 255/48* (2013.01); *C07C 327/44* (2013.01); *C07D 205/04* (2013.01); *C07D 207/273* (2013.01); *C07D 213/40* (2013.01); *C07D 213/75* (2013.01); *C07D 215/48* (2013.01); *C07D 261/04* (2013.01); *C07D 295/192* (2013.01); *C07D 305/06* (2013.01); *C07D 305/08* (2013.01); *C07D 307/52* (2013.01); *C07D 307/79* (2013.01); *C07D 309/14* (2013.01); *C07D 331/04* (2013.01); *C07D 333/38* (2013.01); *C07D 333/72* (2013.01); *C07D 409/12* (2013.01); *C07C 2101/02* (2013.01); *C07C 2101/04* (2013.01); *C07C 2101/08* (2013.01); *C07C 2102/50* (2013.01)

(58) Field of Classification Search
CPC ...... A01N 37/34; A01N 37/18; A01N 43/16; A01N 43/44; A01N 43/40; A01N 43/42; A01N 37/30; A01N 43/20; A01N 43/36; A01N 43/08; A01N 47/16; A01N 43/10; A01N 43/80; C07C 255/48; C07C 233/69; C07C 237/22; C07C 255/29; C07C 233/66; C07C 233/65; C07C 327/44; C07C 255/46; C07C 2101/08; C07C 2102/50; C07C 2101/04; C07C 2101/02; C07D 305/06; C07D 307/79; C07D 215/48; C07D 333/38; C07D 333/72; C07D 213/40; C07D 295/192; C07D 213/75; C07D 307/52; C07D 331/04; C07D 261/04; C07D 207/273; C07D 309/14; C07D 205/04; C07D 409/12; C07D 305/08
See application file for complete search history.

(56) References Cited

U.S. PATENT DOCUMENTS 5,298,527 A     3/1994  Grammenos et al.
6,812,229 B1   11/2004  Ozaki et al.
(Continued)

FOREIGN PATENT DOCUMENTS

DE    WO 2011054436 A2 *  5/2011 ............. A01N 37/18
WO    WO 2011/054436 A2   5/2011
(Continued)

Primary Examiner — Nyeemah A Grazier
Assistant Examiner — Amanda L Aguirre
(74) Attorney, Agent, or Firm — Elizabeth A. McGraw

(57) ABSTRACT

The present invention relates to new compounds of formula (I) wherein the variables have the meaning as indicated in the claims; in free form and in salt form; and optionally the enantiomers and geometrical isomers thereof. The compounds of formula (I) are useful in the control of parasites, in particular ectoparasites, in and on vertebrates.

(I)

13 Claims, No Drawings

(51) Int. Cl.

| | | |
|---|---|---|
| *A01N 43/10* | (2006.01) | |
| *A01N 43/16* | (2006.01) | |
| *A01N 43/20* | (2006.01) | |
| *A01N 43/36* | (2006.01) | |
| *A01N 43/40* | (2006.01) | |
| *A01N 43/42* | (2006.01) | |
| *A01N 43/44* | (2006.01) | |
| *A01N 43/80* | (2006.01) | |
| *A01N 47/16* | (2006.01) | |
| *C07D 213/75* | (2006.01) | |
| *C07D 309/14* | (2006.01) | |
| *C07D 215/48* | (2006.01) | |
| *C07D 331/04* | (2006.01) | |
| *C07D 333/38* | (2006.01) | |
| *C07D 333/72* | (2006.01) | |
| *C07D 409/12* | (2006.01) | |
| *C07D 261/04* | (2006.01) | |
| *C07D 205/04* | (2006.01) | |
| *C07D 207/273* | (2006.01) | |
| *C07D 295/192* | (2006.01) | |
| *C07D 213/40* | (2006.01) | |
| *C07D 305/08* | (2006.01) | |
| *C07D 307/52* | (2006.01) | |
| *C07D 307/79* | (2006.01) | |
| *C07C 255/46* | (2006.01) | |
| *C07C 327/44* | (2006.01) | |
| *C07C 233/65* | (2006.01) | |
| *C07C 255/29* | (2006.01) | |
| *C07C 233/69* | (2006.01) | |
| *C07C 237/22* | (2006.01) | |

(56) References Cited

U.S. PATENT DOCUMENTS

| | | | |
|---|---|---|---|
| 8,889,878 B2 | 11/2014 | Heil et al. | |
| 2011/0105532 A1* | 5/2011 | Heil | A01N 37/18 514/255.06 |
| 2011/0245274 A1* | 10/2011 | Nanchen | A01N 43/80 514/256 |
| 2012/0035122 A1* | 2/2012 | Vaillancourt | A01N 43/80 514/30 |
| 2012/0077765 A1* | 3/2012 | Curtis | C07D 261/04 514/30 |
| 2015/0065343 A1* | 3/2015 | Bindschaedler | A01N 43/10 504/100 |

FOREIGN PATENT DOCUMENTS

| | | | | |
|---|---|---|---|---|
| WO | WO 2013/149940 A1 | 10/2013 | | |
| WO | 2013/167333 | 11/2013 | | |
| WO | WO 2013167633 A1 * | 11/2013 | | A01N 43/10 |

\* cited by examiner

(HETERO) ARYLACRYLAMIDES FOR THE CONTROL OF ECTOPARASITES

The present invention relates to novel pesticides, to a process for the preparation thereof and to their use in the control of ectoparasites, especially insects and acari, on non-human animals, especially productive livestock and domestic animals, and furthermore pesticidal compositions which contain one or more of these compounds

BACKGROUND OF THE INVENTION

PCT Patent Publication WO 2011/054436 discloses cinnamides of Formula (A) as plant insecticides

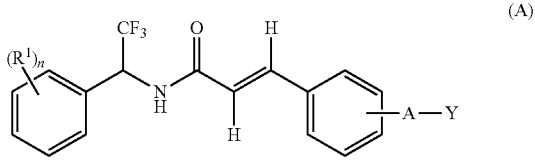

(A)

wherein, inter alia, $R^1$ is halogen and A-Y may represent heteroaryl or a variety of different side chains. The compounds are mainly used in the control of invertebrate pests in agronomic environments. Many products are commercially available for these purposes, but the need continues for new compounds that are more effective, less costly, less toxic, environmentally safer or have different modes of action. It now has been surprisingly found that novel derivatives with a modified heterocyclic side chain have superior properties in the control of pests.

SUMMARY OF THE INVENTION

The present invention according to one object relates to a compound of formula

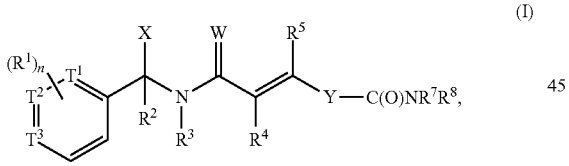

(I)

including all geometric and stereoisomers, N-oxides, S-oxides, salts and prodrugs thereof, wherein $T^1$, $T^2$ and $T^3$ are each independently $C(R^0)$ or N, where the number of nitrogen atoms in $T^1$-$T^3$ is 0 to 2;
$R^0$ is H or $R^1$; n is 1, 2 or 3;
$R^1$ is halogen, cyano (—CN), nitro (—$NO_2$), $C_1$-$C_6$-alkyl, $C_3$-$C_6$-cycloalkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, N-mono or N,N-di-$C_1$-$C_6$-alkylamino, $C_1$-$C_6$ alkoxycarbonyl, $C_1$-$C_6$-alkylcarbonyl, aminosulfonyl, $C_1$-$C_6$-alkylaminosulfonyl, $C_1$-$C_6$-alkylsulfonylamino or phenyl which is unsubstituted or substituted by halogen, cyano, nitro, $C_1$-$C_4$-haloalkyl, $C_1$-$C_4$-haloalkoxy or $C_1$-$C_4$-haloalkylthio; or
$R^1$ is a $C_1$-$C_4$ carbon chain which optionally contains 1-2 heteroatoms from the group of N, S, O, which is bonded to two adjacent ring positions and which forms an aliphatic, aromatic, heteroaromatic or heterocyclic ring which is optionally mono- or polysubstituted by $C_1$-$C_6$-alkyl or halogen, in which case n is 2;
X is $C_1$-$C_6$-alkyl, $C_1$-$C_4$-alkoxy-$C_1$-$C_6$-alkyl, $C_1$-$C_6$ alkoxycarbonyl, $C_1$-$C_6$-haloalkyl, $C_3$-$C_6$-cycloalkyl or $C_3$-$C_6$-halocycloalkyl;
$R^2$ is hydrogen, cyano, hydroxyl, $C_1$-$C_6$-alkyl, $C_2$-$C_6$-alkenyl, $C_2$-$C_6$-alkynyl, $C_1$-$C_6$-alkoxy or $C_3$-$C_6$-cycloalkyl,
$R^3$ is hydrogen, $C_1$-$C_6$-alkyl or $C_1$-$C_6$-alkylcarbonyl;
$R^4$ and $R^5$ are each independently of the other hydrogen, halogen, $C_1$-$C_6$-alkyl or $C_1$-$C_6$-alkoxy;
Y is a radical of formula

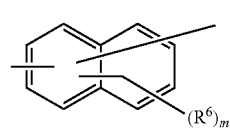

(IIa)

(IIb)

(IIc)

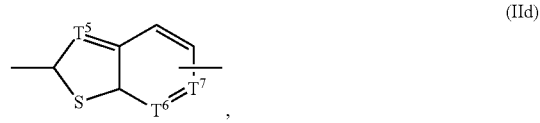

(IId)

(IIe)

or

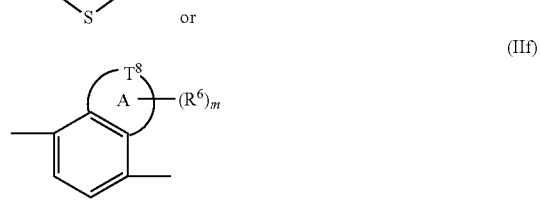

(IIf)

where the second (right-hand) connection site in each case is connected to the $C(O)NR^7R^8$ moiety;
m is an integer 0, 1 or 2; m1 is an integer 0 or 1;
$R^6$ is halogen, cyano, nitro, $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl, $C_4$-$C_7$-cycloalkylalkyl, $C_1$-$C_6$-alkoxy, $C_1$-$C_6$-alkylcarbonyl or $C_1$-$C_6$-alkoxycarbonyl;
A is an annulated 5- or 6-membered heteroaromatic ring comprising $T^8$;
$T^4$ is S or O; $T^5$ is N, CH or $C(CH_3)$; $T^6$ and $T^7$ are each independently CH or N where the number of nitrogen atoms in $T^6$-$T^7$ is 0 or 1; $T^8$ is N or O;
$R^7$ is H, $C_1$-$C_6$-alkyl which is unsubstituted or substituted by halogen, $C_1$-$C_4$-alkoxy, $C_1$-$C_2$-alkylthio, cyano, nitro, amino or N-mono- or N,N-di-$C_1$-$C_4$alkylamino, or is $C_2$-$C_4$-alkenyl, $C_2$-$C_4$-alkynyl or $C_3$-$C_6$-cycloalkyl;

$R^8$ is H; a group —CH=N—$OR^9$; a radical Q; a radical $Q^1$; or is $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl, $C_4$-$C_7$-cycloalkylalkyl, $C_5$-$C_{10}$-bicyclo-alkylene or $C_3$-$C_6$-cycloalkanone which is each unsubstituted or substituted in the alkyl, cycloalkyl, alkenyl or alkynyl moiety by halogen, hydroxy, carboxy (COOH), $C_1$-$C_4$-alkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-alkylsulfonyl, cyano, nitro, amino, N-mono- or N,N-di-$C_1$-$C_6$-alkylamino, $C_3$-$C_6$-cycloalkyl-amino, $C_1$-$C_6$-alkoxycarbonyl, $C_2$-$C_6$-alkylcarbonyl, $C_1$-$C_6$-alkylcarbonylamino, aminosulfonyl, N-mono- or N,N, di-$C_1$-$C_4$-alkylaminosulfonyl, a group —C(W')$NR^9R^{10}$ or a radical Q';

or $R^7$ and $R^8$ together are a group =C($R^{11}$)—$NR^{12}R^{13}$ or =C($R^{11}$)—C($NH_2$)—$OR^{12}$); or $R^7$ and $R^8$ together with the N-atom to which they are attached, form a 3- to 7-membered ring which optionally contains a further heteroatom selected from the group consisting of N, S and O, and which ring is further unsubstituted or mono- or polysubstituted by $C_1$-$C_2$-alkyl, $C_1$-$C_2$-haloalkyl, $C_1$-$C_2$-alkoxy, hydroxy, halogen, cyano, nitro, N,N-di-$C_1$-$C_2$-alkylaminomethyl or N,N-di-$C_1$-$C_2$-alkylaminocarbonylmethyl;

Q and Q' are each independently a $C_6$-$C_{10}$-aryl, an aliphatic or aromatic 4-, 5- or 6-membered heterocyclic ring, or an aliphatic or aromatic 8-, 9- or 10-membered fused heterobicyclic ring, each of them being unsubstituted or mono- or polysubstituted by halogen, hydroxy, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_2$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, cyano, nitro, amino, N-mono- or N,N-di-$C_1$-$C_6$-alkylamino, $C_3$-$C_6$-cycloalkylamino, COOH, $C_1$-$C_6$-alkoxycarbonyl, $C_2$-$C_6$-alkylcarbonyl, $C_1$-$C_6$-alkylcarbonylamino, aminocarbonyl, N-mono- or N,N-di-$C_1$-$C_6$-alkylaminocarbonyl, aminosulfonyl, N-mono- or N,N, di-$C_1$-$C_4$-alkylaminosulfonyl, unsubstituted or halogen- or nitro-substituted phenyl-$C_1$-$C_4$-alkyl, 5- or 6-membered heterocyclyl-$C_1$-$C_4$-alkyl or a radical Q";

Q" is a $C_6$-$C_{10}$-carbocyclic ring or a 4-, 5- or 6-membered heterocyclic ring, each of them being aromatic or not, each of them being unsubstituted or mono- or polysubstituted by halogen, hydroxy, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, cyano, nitro, amino, N-mono- or N,N-di-$C_1$-$C_6$-alkylamino, $C_3$-$C_6$-cycloalkylamino, COOH, $C_1$-$C_6$-alkoxycarbonyl, $C_2$-$C_6$-alkylcarbonyl, $C_1$-$C_6$-alkylcarbonyl-amino, aminocarbonyl, N-mono- or N,N-di-$C_1$-$C_6$-alkylaminocarbonyl, aminosulfonyl, or N-mono- or N,N, di-$C_1$-$C_4$-alkylaminosulfonyl;

$Q^1$ is a radical

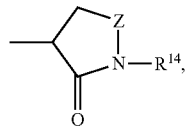

wherein Z is O or $CH_2$ and $R^{14}$ is H, $C_1$-$C_4$-alkyl, or $C_1$-$C_4$-haloalkyl, $R^9$ is H or $C_1$-$C_6$-alkyl;

$R^{10}$ is H, $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl or $C_4$-$C_7$-cycloalkylalkyl, which is each unsubstituted or substituted in the alkyl, alkenyl, alkynyl or cycloalkyl moiety by halogen, cyano, nitro, hydroxy, carboxy (COOH), $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-alkylsulfonyl, amino, N-mono- or N,N-di-$C_1$-$C_6$-alkylamino, $C_3$-$C_6$-cycloalkylamino, $C_1$-$C_6$-alkoxycarbonyl, $C_2$-$C_6$-alkylcarbonyl, $C_1$-$C_6$-alkylcarbonylamino, aminocarbonyl, N-mono- or N,N-di-$C_1$-$C_6$-alkylaminocarbonyl, aminosulfonyl, N-mono- or N,N, di-$C_1$-$C_4$-alkylaminosulfonyl or a radical Q";

$R^{11}$ is H $C_1$-$C_6$-alkyl or $C_1$-$C_6$-alkoxy, $R^{12}$ and $R^{13}$ are each independently of the other $C_1$-$C_6$-alkyl, and W and W' are each independently O or S.

This invention also provides a composition comprising a compound of formula (I), an N-oxide or a salt thereof, and at least one additional component selected from the group consisting of a surfactant, a solid diluent and a liquid diluent.

In one embodiment, this invention also provides a composition for controlling parasites, in particular ectoparasites, comprising a biologically effective amount of a compound of formula (I), an N-oxide, S-oxide or a salt thereof, and at least one additional component selected from the group consisting of a surfactant, a solid diluent and a liquid diluent, said composition optionally further comprising a biologically effective amount of at least one additional biologically active compound or agent.

This invention further provides the composition described above in the form of a bait composition wherein the solid diluent and/or the liquid diluent comprises one or more food materials, said composition optionally comprising an attractant and/or a humectant.

This invention further provides a trap device for controlling parasites, in particular ectoparasites, comprising said bait composition and a housing adapted to receive said bait composition, wherein the housing has at least one opening sized to permit the parasites to pass through the opening. so the invertebrate pest can gain access to said bait composition from a location outside the housing, and wherein the housing is further adapted to be placed in or near a locus of potential or known activity for the parasites pest.

This invention also provides a method for controlling parasites comprising contacting the parasites or their environment with a biologically effective amount of a compound of formula (I), an N-oxide, S-oxide or a salt thereof, (e.g., as a composition described herein). This invention also relates to such method wherein the parasites or their environment are contacted with a composition comprising a biologically effective amount of a compound of formula (I), an N-oxide, S-oxide or a salt thereof, and at least one additional component selected from the group consisting of a surfactant, a solid diluent and a liquid diluent, said composition optionally further comprising a biologically effective amount of at least one additional biologically active compound or agent.

This invention also provides a composition for protecting an animal from an parasitic pest comprising a parasiticidally effective amount of a compound of formula (I) an N-oxide or a salt thereof, and at least one carrier. The present invention further provides the composition described above in a form for oral administration. This invention also provides a method for protecting an animal from a parasitic pest comprising administering to the animal a parasiticidally effective amount of a compound of formula (I), an N-oxide or a salt thereof.

DETAILS OF THE INVENTION

In the above recitations, the term "alkyl", used either alone or in compound words such as "alkylthio", "haloalkylthio", "haloalkyl", "N-alkylamino" or "N,N-di-alkylamino includes straight-chain or branched alkyl, such as, methyl, ethyl, n-propyl, i-propyl, n-, iso-, sec.- or tert.-butyl or the different pentyl or hexyl isomers.

"Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl.

"Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

The term "alkoxy" used either alone or in compound words such as "haloalkoxy", "alkoxycarbonyl" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers.

"Alkylsulfinyl" includes both enantiomers of an alkylsulfinyl group. Examples of "alkylsulfinyl" include $CH_3S(O)-$, $CH_3CH_2S(O)-$, $CH_3CH_2CH_2S(O)-$, $(CH_3)_2CHS(O)-$ and the different butylsulfinyl, pentylsulfinyl and hexylsulfinyl isomers.

"Alkylcarbonyl" denotes a straight-chain or branched alkyl moieties bonded to a $C(=O)$ moiety. Examples of "alkylcarbonyl" include $CH_3C(=O)-$, $CH_3CH_2CH_2C(=O)-$ and $(CH_3)_2CHC(=O)-$. Examples of "alkoxycarbonyl" include $CH_3OC(=O)-$, $CH_3CH_2OC(=O)$, $CH_3CH_2CH_2OC(=O)-$, $(CH_3)_2CHOC(=O)-$ and the different butoxy- or pentoxycarbonyl isomers, for example tert.-butoxycarbonyl (Boc). Examples of "N-mono- or N,N-di-alkylaminocarbonyl" include "N-methylaminocarbonyl", "N-ethylaminocarbonyl, N-methyl-N-ethylaminocarbonyl, N,N-di-methylaminocarbonyl or N,N-di-ethylaminocarbonyl. Examples of "alkylcarbonylamino" include", "methylcarbonylamino" or "ethylcarbonylamino".

Examples of "alkylsulfonyl" include $CH_3S(O)_2-$, $CH_3CH_2S(O)_2-$, $CH_3CH_2CH_2S(O)_2-$, $(CH_3)_2CHS(O)_2-$, and the different butylsulfonyl, pentylsulfonyl and hexylsulfonyl isomers.

Examples of "N-mono- or N,N-di-alkylaminosulfonyl" include "N-methylaminosulfonyl", "N-ethylaminosulfonyl, N-methyl-N-ethylaminosulfonyl, N,N-di-methylaminosulfonyl or N,N-di-ethylaminosulfonyl. Examples of "alkylsulfonylamino" include", "methylsulfonylamino" or "ethylsulfonylamino".

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methycyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

Cycloalkanone includes, for example, cyclopropanone, cyclobutanone, cyclopentanone and cyclohexanone, in particular cyclohexanone.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C-$, $ClCH_2-$, $CF_3CH_2-$ and $CF_3CCl_2-$. The terms "halocycloalkyl", "haloalkoxy", "haloalkylthio", and the like, are defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$. Examples of "haloalkylsulfinyl" include $CF_3S(O)-$, $CCl_3S(O)-$, $CF_3CH_2S(O)-$ and $CF_3CF_2S(O)-$. Examples of "haloalkylsulfonyl" include $CF_3S(O)_2-$, $CCl_3S(O)_2-$, $CF_3CH_2S(O)_2-$ and $CF_3CF_2S(O)_2-$.

The total number of carbon atoms in a substituent group is indicated by the "$C_i$-$C_j$" prefix where i and j are integers. For example, $C_1$-$C_4$ alkylsulfonyl designates methylsulfonyl through butylsulfonyl; $C_2$-alkoxyalkyl designates $CH_3OCH_2$; $C_3$-alkoxyalkyl designates, for example, $CH_3CH(OCH_3)$, $CH_3OCH_2CH_2$ or $CH_3CH_2OCH_2$; and $C_4$-alkoxyalkyl designates the various isomers of an alkyl group substituted with an alkoxy group containing a total of four carbon atoms, examples including $CH_3CH_2CH_2OCH_2$ and $CH_3CH_2OCH_2CH_2-$.

When a compound is substituted with a substituent bearing a subscript that indicates the number of said substituents can exceed 1, said substituents (when they exceed 1) are independently selected from the group of defined substituents, e.g., $(R_2)_n$, n is 1 or 2. "Aromatic" indicates that each of the ring atoms is essentially in the same plane and has ap-orbital perpendicular to the ring plane, and in which (4n+2) π electrons, where n is a positive integer, are associated with the ring to comply with Hückel's rule.

The terms "heterocyclic ring" or "heterocycle" denote a ring in which at least one atom forming the ring backbone is not carbon, e.g., nitrogen, oxygen sulfur or a group $S(O)$ or $S(O_2)$. Typically a heterocyclic ring contains no more than 4 nitrogens, no more than 2 oxygens and no more than 2 sulfurs. In addition, the heterocyclic ring may contain a group $-C(O)-$, $-S(O)-$ or $-S(O_2)-$. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring", "aromatic heterocyclic ring". Unless otherwise indicated, heterocyclic rings and ring systems can be attached through any available carbon or nitrogen by replacement of a hydrogen on said carbon or nitrogen.

According to a preferred embodiment the invention relates to a compound of the above formula (I), including all geometric and stereoisomers, N-oxides, S-oxides, salts and prodrugs thereof, wherein $T^1$, $T^2$ and $T^3$ are each independently $C(R^0)$ or N, where the number of nitrogen atoms in $T^1$-$T^3$ is 0 to 2;

$R^0$ is H or $R^1$; n is 1, 2 or 3;

$R^1$ is halogen, cyano (—CN), nitro (—$NO_2$), $C_1$-$C_6$-alkyl, $C_3$-$C_6$-cycloalkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, N-mono- or N,N-di-$C_1$-$C_6$-alkylamino, $C_1$-$C_6$ alkoxycarbonyl, $C_1$-$C_6$-alkylcarbonyl, aminosulfonyl, $C_1$-$C_6$-alkylaminosulfonyl or $C_1$-$C_6$-alkylsulfonylamino; or $R^1$ is a $C_1$-$C_4$ carbon chain which optionally contains 1-2 heteroatoms from the group of N, S, O, which is bonded to two adjacent ring positions and which forms an aliphatic, aromatic, heteroaromatic or heterocyclic ring which is optionally mono- or polysubstituted by $C_1$-$C_6$-alkyl or halogen, in which case n is 2;

X is $C_1$-$C_6$-haloalkyl or $C_3$-$C_6$-halocycloalkyl;
$R^2$ is hydrogen, cyano, hydroxyl, $C_1$-$C_6$-alkyl, $C_2$-$C_6$-alkenyl, $C_2$-$C_6$-alkynyl, $C_1$-$C_6$-alkoxy or $C_3$-$C_6$-cycloalkyl,
$R^3$ is hydrogen, $C_1$-$C_6$-alkyl or $C_1$-$C_6$-alkylcarbonyl;
$R^4$ and $R^5$ are each independently of the other hydrogen, halogen, $C_1$-$C_6$-alkyl or $C_1$-$C_6$-alkoxy;
Y is a radical of formula

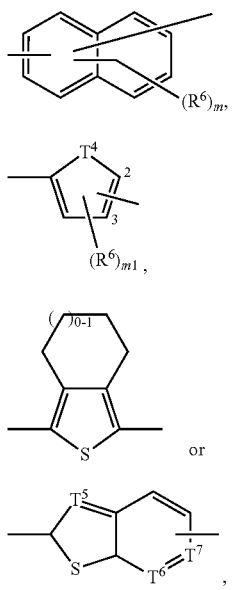

where the second (right-hand) connection site in each case is connected to the $C(O)NR^7R^8$ moiety;
m is an integer 0, 1 or 2; m1 is an integer 0 or 1;
$R^6$ is halogen, cyano, nitro, $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl, $C_4$-$C_7$-cycloalkylalkyl, $C_1$-$C_6$-alkoxy, $C_1$-$C_6$-alkylcarbonyl or $C_1$-$C_6$-alkoxycarbonyl;
$T^4$ is S or O; $T^5$ is N, CH or $C(CH_3)$; $T^6$ and $T^7$ are each independently CH or N where the number of nitrogen atoms in $T^6$-$T^7$ is 0 or 1;
$R^7$ is H, $C_1$-$C_6$-alkyl which is unsubstituted or substituted by halogen, $C_1$-$C_4$-alkoxy, $C_1$-$C_2$-alkylthio, cyano, nitro, amino or N-mono- or N,N-di-$C_1$-$C_4$alkylamino, or is $C_2$-$C_4$-alkenyl, $C_2$-$C_4$-alkynyl or $C_3$-$C_6$-cycloalkyl;
$R^8$ is H; a group —CH=N—$OR^9$; a radical Q; or is $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl, $C_4$-$C_7$-cycloalkylalkyl or $C_3$-$C_6$-cycloalkanone which is each unsubstituted or substituted in the alkyl, cycloalkyl, alkenyl or alkynyl moiety by halogen, hydroxy, carboxy (COOH), $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-alkylsulfonyl, cyano, nitro, amino, N-mono- or N,N-di-$C_1$-$C_6$-alkylamino, $C_3$-$C_6$-cycloalkylamino, $C_1$-$C_6$-alkoxycarbonyl, $C_2$-$C_6$-alkylcarbonyl, $C_1$-$C_6$-alkylcarbonylamino, aminosulfonyl, N-mono- or N,N, di-$C_1$-$C_4$-alkylaminosulfonyl, a group —C(W') $NR^9R^{10}$ or a radical Q';
or $R^7$ and $R^8$ together are a group =$C(R^{11})$—$NR^{12}R^{13}$ or =$C(R^{11})$—$C(NH_2)$—$OR^{12}$); or
$R^7$ and $R^8$ together with the N-atom to which they are attached, form a 3- to 7-membered ring which optionally contains a further heteroatom selected from the group consisting of N, S and O, and which ring is further unsubstituted or mono- or polysubstituted by $C_1$-$C_2$-alkyl, $C_1$-$C_2$-haloalkyl, $C_1$-$C_2$-alkoxy, hydroxy, halogen, cyano, nitro, N,N-di-$C_1$-$C_2$-alkylaminomethyl or N,N-di-$C_1$-$C_2$-alkylaminocarbonylmethyl;
Q and Q' are each independently a $C_6$-$C_{10}$-carbocyclic ring, a 4-, 5- or 6-membered heterocyclic ring, or a 8-, 9- or 10-membered fused hetero-bicyclic ring, each of them being aromatic or not, each of them being unsubstituted or mono- or polysubstituted by halogen, hydroxy, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_2$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, cyano, nitro, amino, N-mono- or N,N-di-$C_1$-$C_6$-alkylamino, $C_3$-$C_6$-cycloalkyl-amino, COOH, $C_1$-$C_6$-alkoxycarbonyl, $C_2$-$C_6$-alkylcarbonyl, $C_1$-$C_6$-alkylcarbonylamino, aminocarbonyl, N-mono- or N,N-di-$C_1$-$C_6$-alkylaminocarbonyl, aminosulfonyl, N-mono- or N,N, di-$C_1$-$C_4$-alkylaminosulfonyl, unsubstituted or halogen- or nitro-substituted phenyl-$C_r$$C_4$-alkyl, 5- or 6-membered heterocyclyl-$C_1$-$C_4$-alkyl or a radical Q";
Q" is a $C_6$-$C_{10}$-carbocyclic ring or a 4-, 5- or 6-membered heterocyclic ring, each of them being aromatic or not, each of them being unsubstituted or mono- or polysubstituted by halogen, hydroxy, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, cyano, nitro, amino, N-mono- or N,N-di-$C_1$-$C_6$-alkylamino, $C_3$-$C_6$-cycloalkylamino, COOH, $C_1$-$C_6$-alkoxycarbonyl, $C_2$-$C_6$-alkylcarbonyl, $C_1$-$C_6$-alkylcarbonylamino, aminocarbonyl, N-mono- or N,N-di-$C_1$-$C_6$-alkylaminocarbonyl, aminosulfonyl, or N-mono or N,N, di-$C_1$-$C_4$-alkylaminosulfonyl;
$R^9$ is H or $C_1$-$C_6$-alkyl;
$R^{10}$ is H, $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl or $C_4$-$C_7$-cycloalkylalkyl, which is each unsubstituted or substituted in the alkyl, alkenyl, alkynyl or cycloalkyl moiety by halogen, cyano, nitro, hydroxy, carboxy (COOH), $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-alkylsulfonyl, amino, N-mono- or N,N-di-$C_1$-$C_6$-alkylamino, $C_3$-$C_6$-cycloalkylamino, $C_1$-$C_6$-alkoxycarbonyl, $C_2$-$C_6$-alkylcarbonyl, $C_1$-$C_6$-alkylcarbonylamino, aminocarbonyl, N-mono- or N,N-di-$C_1$-$C_6$-alkylaminocarbonyl, aminosulfonyl, N-mono- or N,N, di-$C_1$-$C_4$-alkylaminosulfonyl or a radical Q";
$R^{11}$ is H $C_1$-$C_6$-alkyl or $C_1$-$C_6$-alkoxy,
$R^{12}$ and $R^{13}$ are each independently of the other $C_1$-$C_6$-alkyl, and
W and W' are each independently O or S.

The following meanings and preferences apply to the variables contained in formula (I):

The number of nitrogen atoms in $T^1$-$T^3$ is preferably 0 or 1, in particular 0; accordingly two or three, in particular all three, of $T^1$-$T^3$ are a radical $R^0$.

If either $T^1$ and $T^2$ or $T^2$ and $T^3$ are each $C(R^0)$, $R^0$ is each W and the two $R^1$ radicals form a carbon chain which is bonded to two adjacent ring positions, this is preferably a $C_4H_4$ chain and the resulting ring formed is a phenyl ring.

The variable n is preferably 1 or 2, in particular 1.

Each $R^1$ is independently of the other preferably halogen, cyano, nitro, $C_1$-$C_2$-alkyl, $C_1$-$C_2$-haloalkyl, $C_1$-$C_2$-haloalkylthio, $C_1$-$C_2$-alkoxy, $C_1$-$C_2$ haloalkoxy or $C_1$-$C_2$-alkylsulfonyl, more preferably halogen, $CH_3$, $CF_3$, $OCF_3$, $SCF_3$ or $SO_2CH_3$, especially halogen or $CF_3$, in particular chlorine, fluorine or $CF_3$. According to one embodiment n is 1 and $R_1$ is $CF_3$. According to a further embodiment, n is 2 and one $R_1$ is chlorine, fluorine or $CF_3$ and the other $R_1$ is chlorine or fluorine. According to still a further embodiment n is 3 and the three $R_1$ are each independently chlorine or fluorine. According to a a further embodiment, $R^1$ is phenyl which is unsubstituted or substituted by 1 to 3 same or different radicals selected from the group consisting of chlorine fluorine and $CF_3$.

X is preferably $C_1$-$C_6$-haloalkyl, more preferably $C_1$-$C_2$-haloalkyl, and in particular $CF_3$.

$R^2$ is preferably H or $C_1$-$C_4$-alkyl, more preferably H or $C_1$-$C_2$-alkyl, even more preferably H or methyl, in particular H.

$R^3$ is preferably H or $C_1$-$C_4$-alkyl, more preferably H or $C_1$-$C_2$-alkyl, even more preferably H or methyl, in particular H.

W is preferably O.

$R^4$ and $R^5$ are each independently preferably H or $C_1$-$C_4$-alkyl, more preferably H or $C_1$-$C_2$-alkyl, even more preferably H or methyl, in particular each H. According to a preferred embodiment, $R^4$ is H and $R^5$ is H or methyl, in particular H.

If Y is a radical of formula (IIf), the ring A may be, for example a 6-membered heteroaromatic ring wherein $T^8$ which is N and m is 0. According to a further embodiment of the invention, A is a 5-membered ring, wherein $T^8$ is O, m is 0 or 1 and $R^6$ is $C_1$-$C_2$-alkyl. Examples of suitable radicals (IIf) are a radical

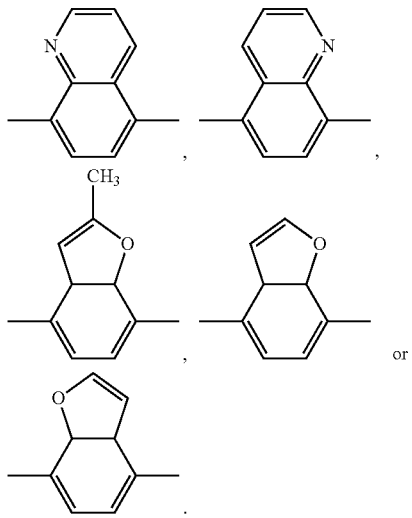

Preferred embodiments of Y according to the invention are:

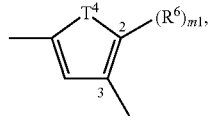

(IIa')

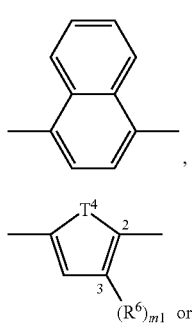

(IIb')

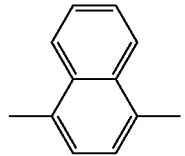

(IIb*)

wherein $T^4$ is S or O, in particular S, m1 is 0 or 1, and $R^6$ is halogen, cyano or $C_1$-$C_4$-alkyl, preferably $C_1$-$C_2$-alkyl and in particular methyl, and where the second (right-hand) connection site is in each case connected to the $C(O)NR^7R^8$ moiety.

Preferred embodiments of Y according to the present invention are:

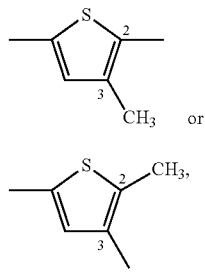

(IIa')

(IIb'')

(IIb**)

where the second (right-hand) connection site in each case is connected to the $C(O)NR^7R^8$ moiety.

$R^7$ is preferably H, $C_1$-$C_4$-alkyl or $C_3$-$C_6$-cycloalkyl, more preferably H, $C_1$-$C_2$-alkyl or cyclopropyl, even more preferably H or $C_1$-$C_2$-alkyl, and in particular H.

$R^9$ is preferably H or $C_1$-$C_2$-alkyl, and in particular H or methyl.

$R^{10}$ is preferably H, $C_1$-$C_2$-alkyl

According to one embodiment of the invention, Q and Q' each independently may be a $C_6$-$C_{10}$-carbocyclic ring system, for example phenyl, naphthyl, tetrahydronaphthyl, indanyl, indenyl, hydrindanyl or octahydro-pentalen, in particular phenyl, which is each unsubstituted or substituted by one or more same or different substituents selected from the group of substituents as mentioned above. Q and Q' as carbocyclic ring radical are each preferably phenyl which is unsubstituted or substituted by 1 to 4, preferably 1 to 3 and in particular 1 or 2 same or different substituents selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, cyano, nitro, aminocarbonyl, $C_1$-$C_4$-alkoxycarbonyl, sulfonylamino, $C_2$-$C_3$-alkanoyl and unsubstituted or halogen-, $C_1$-$C_4$-alkyl-, $C_1$-$C_4$-haloalkyl-, $C_1$-$C_4$-alkoxy-, $C_1$-$C_4$-haloalkoxy-, cyano- or nitro-substituted phenyl, benzyl, benzoyl and phenoxy. Q and Q' as carbocyclic ring radical are each more preferably phenyl, which is unsubstituted or substituted by 1 to 3, in particular 1 or 2, same or different substituents selected from the group consisting of halogen, $C_1$-$C_2$-alkyl, $C_1$-$C_2$-haloalkyl, $C_1$-$C_2$- alkoxy, $C_1$-$C_2$-haloalkoxy, $C_1$-$C_2$-haloalkylthio, cyano, nitro, aminocarbonyl and unsubstituted or halogen-, $C_1$-$C_2$-alkyl-, $C_1$-$C_2$-haloalkyl-, $C_1$-$C_2$-alkoxy-, $C_1$-$C_2$-haloalkoxy-, cyano- or nitro-substituted phenyl and phenoxy. Q and Q' as carbocyclic ring radical are each most preferably phenyl, which is unsubstituted or substituted by halogen, $C_1$-$C_2$-alkyl or $C_1$-$C_2$-alkoxy.

According to another embodiment of the invention, Q and Q' are each independently a 4-, 5- or 6-membered heterocyclic ring, which may contain, for example, from 1 to 4, preferably from 1 to 3, same or different heteroatoms selected from N, O, S, S(O) and S(O$_2$), besides one or more C-atoms and optionally a bivalent group —C(O)—. Preferred heteroatoms included in Q or Q' are N, O and S.

The heterocyclic ring Q and Q' may be substituted as mentioned before; preferred substituents are $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, cyano, nitro, $C_1$-$C_4$-alkoxycarbonyl, aminocarbonyl, aminosulfonyl, N-mono- or N,N-di-$C_1$-$C_4$-alkylamino, $C_2$-$C_3$-alkanoyl and unsubstituted or halogen- or $C_1$-$C_4$-alkyl-substituted phenyl, benzyl, benzoyl and phenoxy. Even more preferred substituents of the heterocyclic ring Q and Q' are each selected from the group consisting of halogen, $C_1$-$C_2$-alkyl, cyclopropyl, $C_1$-$C_2$-haloalkyl, $C_1$-$C_2$-alkoxy, $C_1$-$C_2$-haloalkoxy, cyano, nitro, and $C_1$-$C_4$-alkoxycarbonyl, in particular $C_1$-$C_2$-alkyl, $C_1$-$C_2$-haloalkyl, aminocarbonyl and $C_1$-$C_4$-alkoxycarbonyl.

The heterocyclic radical Q and Q' is each independently preferably substituted by 0 to 3, in particular 0, 1 or 2 substituents from the group as defined before for Q and Q'.

Examples of a 5- or 6-membered heteroaromatic ring radical Q and Q' are thienyl, furanyl, pyrrolyl, oxazolyl, isoxazolyl, isoxazolidinyl-3-one, thiazolyl, isothiazolyl, pyrazolyl, imidazolyl, triazolyl, thiadiazolyl, oxadiazolyl, pyridyl, pyridazinyl, pyrimidinyl, pyrazinyl and triazinyl, which are each unsubstituted or substituted as mentioned before including the preferences.

Preferred heteroaromatic radicals Q and Q' are 2- or 3-furanyl, 2- or 3-thienyl, 1-, 2- or 3-pyrrolyl, 1-, 2-, 4- or 5-imidazolyl, 1- or 4-pyrazolyl, 2-, 4- or 5-thiazolyl, 1,2,4-triazol-3- or -4-yl, 1,2,3-triazin-1- or 2-yl, 2- 3- or 4-pyridyl or 4- or 5-pyrimidinyl, each unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano, nitro, aminocarbonyl or $C_1$-$C_4$-alkoxycarbonyl.

Particularly preferred heteroaromatic ring radicals Q and Q' are 2-furanyl, 2-thiazoyl, 2- 3- or 4-pyridyl or 4- or 5-pyrimidinyl, each unsubstituted or substituted by $C_1$-$C_2$-alkyl, $C_1$-$C_2$-haloalkyl and $C_1$-$C_4$-alkoxycarbonyl.

A further group of suitable heterocyclic radicals Q and Q' comprises, for example, a 4-, 5- or 6-membered heteroaliphatic ring having from 1 to 4, preferably from 1 to 3 same or different heteroatoms selected from the group consisting of N, O, S, S(O) and S(O$_2$) which is further unsubstituted or substituted by one or more substituents as defined before for Q and Q' including the preferences given therefore.

Examples of heteroaliphatic rings Q and Q' include oxetanyl, thietanyl, thietanyl-1-oxide, thietanyl-1,1-dioxide, tetrahydrofuranyl, tetrahydrothiophenyl, pyrrolidinyl, 2- or 3-pyrrolidonyl, 1,3-dioxolanyl, 1,2- or 1,3-oxazolidinyl, tetrahydropyranyl, piperidinyl, tetrahydrothiopyranyl, tetrahydrothiopyranyl-1,1-dioxide, morpholinyl, 1,3- or 1,4-dioxanyl, which may each be substituted as mentioned before for Q and Q', preferably by halogen, $C_1$-$C_2$-alkyl, cyclopropyl, $C_1$-$C_2$-haloalkyl, $C_1$-$C_2$-alkoxy, $C_1$-$C_2$-haloalkoxy, cyano, nitro, or $C_1$-$C_4$-alkoxycarbonyl.

A preferred heteroaliphatic ring radical Q and Q' is oxetan-3-yl, thietan-3-yl, thietan-3-yl-1-oxide, thietan-3-yl-1,1-dioxide, or tetrahydrofuran-2- or -3-yl, which is each unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano, nitro or $C_1$-$C_4$-alkoxycarbonyl, in particular each unsubstituted.

Particularly preferred heteroaliphatic ring radicals Q and Q' are oxetan-3-yl, thietan-3-yl, thietan-3-yl-1-oxide, thietan-3-yl-1,1-dioxide, tetrahydrofuran-2-yl and tetrahydrofuran-3-yl.

A suitable fused hetero-bicyclic ring system comprises, for example a 5- or 6-membered heterocyclic ring having from 1 to 4, preferably from 1 to 3 same or different heteroatoms selected from the group consisting of N, O and S, to which is attached an annulated ring; in addition said fused bicyclic system is further unsubstituted or substituted by one or more substituents as defined before for Q including the preferences given. Those rings can be saturated ring or unsaturated rings.

Examples of fused hetero-bicyclic ring systems Q and Q' are indolyl, isoindolyl, benzofuranyl, dihydrobenzofuranyl, thionaphthenyl, dihydrothionaphthenyl, indolyl, dihydroindolyl, benzimidazolyl, benzthiazolyl, benzthiazolyl, chinolinyl, isochinolinyl, chromanyl, chinazolinyl, chinoxalinyl or phthalazinyl and the like.

According to a preferred embodiment of the invention, Q and Q' are each phenyl, 2- or 3-furanyl, 2- or 3-thienyl, 1-, 2- or 3-pyrrolyl, 1-, 2-, 4- or 5-imidazolyl, 1- or 4-pyrazolyl, 2-, 4- or 5-thiazolyl, 1,2,4-triazol-3- or -4-yl, 1,2,3-triazin-1- or 2-yl, 2- 3- or 4-pyridyl, 4- or 5-pyrimidinyl, oxetanyl, thietanyl, thietanyl-1-oxide, thietanyl-1,1-dioxide or tetrahydrofuranyl, which is each unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano, nitro, aminocarbonyl or $C_1$-$C_4$-alkoxycarbonyl.

A particularly preferred radical Q and Q' is unsubstituted or halogen-, $C_1$-$C_2$-alkyl- or $C_1$-$C_2$-alkoxy-substituted phenyl, 2-furanyl, 2-thiazoyl, 2- 3- or 4-pyridyl, 4- or 5-pyrimidinyl, oxetan-3-yl, thietan-3-yl, thietan-3-yl, thietan-3-yl-1-oxide, thietan-3-yl-1,1-dioxide, tetrahydrofuran-2-yl or tetrahydrofuran-3-yl.

Q'' independently has the meaning of Q' as heterocyclic ring or $C_6$-$C_{10}$-carbocyclic ring system, with the exception that Q'' is not substituted by another radical Q'', including the above-given preferences.

A preferred radical $Q^1$, for example, a radical

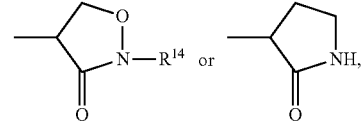

wherein $R^{14}$ is H, methyl, ethyl, $CF_3$ or $CH_2$—$CF_3$.

$R^8$ as alkyl is preferably $C_1$-$C_4$-alkyl which is unsubstituted or substituted by halogen; $C_1$-$C_4$-alkoxy; $C_1$-$C_2$-alkylthio; cyano; nitro; amino; N-mono- or N,N-di-$C_1$-$C_4$-alkylamino; carboxy; $C_1$-$C_2$-alkoxycarbonyl; —C(O)NHR$^{10}$ wherein R$^{10}$ is $C_1$-$C_4$-alkyl, halo-$C_1$-$C_4$-alkyl, cyano-$C_1$-$C_4$-alkyl, $C_2$-$C_4$-alkynyl or $C_3$-$C_6$-cycloalkyl-$C_1$-$C_4$-alkyl; phenyl which is unsubstituted or substituted by halogen, $C_1$-$C_2$-alkyl or $C_1$-$C_2$-alkoxy; or $C_3$-$C_6$-heteroaryl, which is unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano, nitro, aminocarbonyl or $C_1$-$C_4$-alkoxycarbonyl.

$R^8$ as alkyl is more preferably $C_1$-$C_2$-alkyl which is unsubstituted or substituted by halogen; $C_1$-$C_2$-alkoxy; carboxy; $C_1$-$C_2$-alkoxycarbonyl; —C(O)NHR$^{10}$ wherein R$^{10}$ is $C_1$-$C_4$-alkyl, halo-$C_1$-$C_2$-alkyl, cyano-$C_1$-$C_2$-alkyl, $C_2$-$C_3$-alkynyl or cyclopropylmethyl; phenyl which is unsubstituted or substituted by halogen, $C_1$-$C_2$-alkyl or $C_1$-$C_2$-alkoxy; or 2- or 3-furanyl, 2- or 3-thienyl, 1-, 2- or 3-pyrrolyl, 1-, 2-, 4- or 5-imidazolyl, 1- or 4-pyrazolyl, 2-, 4- or 5-thiazolyl, 1,2,4-triazol-3- or -4-yl, 1,2,3-triazin-1- or 2-yl, 2- 3- or 4-pyridyl, 4- or 5-pyrimidinyl, oxetanyl, thietanyl, thietanyl-1-oxide, thietanyl-1,1-dioxide or tetrahydrofuranyl, which is each unsubstituted or substituted by halogen, $C_1$-$C_2$-alkyl, $C_1$-$C_2$-alkoxy or aminocarbonyl.

$R^8$ as alkyl is especially preferably $C_1$-$C_2$-alkyl which is unsubstituted or substituted by chlorine; fluorine; $C_1$-$C_2$-alkoxy; —C(O)NHR$^{10}$ wherein R$^{10}$ is $C_1$-$C_4$-alkyl, 2,2,2-trifluoroethyl, cyanomethyl, propargyl or cyclopropylmethyl; phenyl which is unsubstituted or substituted by halogen, $C_1$-$C_2$-alkyl or $C_1$-$C_2$-alkoxy; 2-furanyl, 2-thiazoyl, 2- 3- or 4-pyridyl, 4- or 5-pyrimidinyl, oxetan-3-yl, thietan-3-yl, thietan-3-yl-1-oxide, thietan-3-yl-1,1-dioxide, tetrahydrofuran-2-yl or tetrahydrofuran-3-yl.

$R^8$ as alkenyl is preferably $C_2$-$C_4$-alkenyl, in particular allyl.

$R^8$ as alkynyl is preferably $C_2$-$C_4$-alkynyl, in particular propargyl.

$R^8$ as cycloalkyl is, for example $C_3$-$C_5$-cycloalkyl preferably $C_3$-$C_4$-cycloalkyl, in particular cyclopropyl. A preferred cycloalkyl radical $R^8$ is unsubstituted or substituted by halogen, cyano or $C_1$-$C_2$-alkyl. Examples of suitable cycloalkyl radicals $R^8$ are cyclopropyl, 1-cyano-cycloprop-1-yl, 2-fluoro-cycloprop-1-yl, cyclobutyl, 3-fluorocyclobut-1-yl, 3,3-difluoro-cyclobut-1-yl, 1-CF$_3$-cyclobut-1-yl, 1-methyl-cyclobut-1-yl, 1-cyano-cyclobut-1-yl, cyclopentyl. A preferred cycloalkyl radical $R^8$ is cyclopropyl. $R^8$ as cycloalkylalkyl is preferably $C_3$-$C_6$-cycloalkylmethyl, more preferably $C_3$-$C_4$-cycloalkylmethyl, in particular cyclopropylmethyl. $R^8$ as alkylcycloalkyl is preferably $C_5$-$C_6$-cycloalkyl which is substituted by 1 to 3 methyl groups. A $C_5$-$C_{10}$-bicycloalkylene radicals $R^8$ is, for example a radical of formula

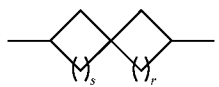

wherein s and r are each independently an integer 1 or 2.

$R^8$ is preferably
(i) phenyl, which is unsubstituted or substituted by 1 or 2, same or different substituents selected from the group consisting of halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, cyano, nitro, aminocarbonyl and unsubstituted or halogen-, $C_1$-$C_2$-alkyl-, $C_1$-$C_2$-haloalkyl-, $C_1$-$C_2$-alkoxy-, $C_1$-$C_2$-haloalkoxy-, cyano- or nitro-substituted phenyl and phenoxy; or is
(ii) 2- or 3-furanyl, 2- or 3-thienyl, 1-, 2-, 4- or 5-imidazolyl, 1- or 4-pyrazolyl, 2-, 4- or 5-thiazolyl, 1,2,4-triazol-3- or -4-yl, 1,2,3-triazin-1- or 2-yl, 2- 3- or 4-pyridyl or 4- or 5-pyrimidinyl, which is each unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano, nitro, aminocarbonyl or $C_1$-$C_4$-alkoxycarbonyl; or is
(iii) oxetanyl, thietanyl, thietanyl-1 oxide, thietanyl-1,1-dioxide, tetrahydrofuranyl, tetrahydrothiophenyl, pyrrolidinyl, 2- or 3-pyrrolidonyl, 1,3-dioxolanyl, 1,2- or 1,3-oxazolidinyl, tetrahydropyranyl, piperidinyl, tetrahydrothiopyranyl, tetrahydrothiopyranyl-1,1-dioxid, morpholinyl, or 1,3- or 1,4-dioxanyl, which is each unsubstituted or substituted by halogen, $C_1$-$C_2$-alkyl, cyclopropyl, $C_1$-$C_2$-haloalkyl, $C_1$-$C_2$-alkoxy, $C_1$-$C_2$-haloalkoxy, cyano, nitro, or $C_1$-$C_4$-alkoxycarbonyl; or is
(iv) $C_1$-$C_2$-alkyl which is unsubstituted or substituted by halogen; $C_1$-$C_2$-alkoxy; carboxy; $C_1$-$C_2$-alkoxycarbonyl; a radical —C(O)NHR$^{10}$ wherein R$^{10}$ is $C_1$-$C_4$-alkyl, halo-$C_1$-$C_2$-alkyl, cyano-$C_1$-$C_2$-alkyl, $C_2$-$C_3$-alkynyl or cyclopropylmethyl; phenyl which is unsubstituted or substituted by halogen, $C_1$-$C_2$-alkyl or $C_1$-$C_2$-alkoxy; or a heterocyclic ring selected from 2- or 3-furanyl, 2- or 3-thienyl, 1-, 2- or 3-pyrrolyl, 1-, 2-, 4- or 5-imidazolyl, 1- or 4-pyrazolyl, 2-, 4- or 5-thiazolyl, 1,2,4-triazol-3- or -4-yl, 1,2,3-triazin-1- or 2-yl, 2- 3- or 4-pyridyl, 4- or 5-pyrimidinyl, oxetanyl, thietanyl, thietanyl-1-oxide, thietanyl-1,1-dioxide and tetrahydrofuranyl, which is each unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano, nitro, aminocarbonyl or $C_1$-$C_4$-alkoxycarbonyl; or is
(v) $C_2$-$C_4$-alkenyl; (vi) $C_2$-$C_4$-alkynyl; (vii) $C_3$-$C_6$-cycloalkyl; or (viii) $C_3$-$C_6$-cycloalkylmethyl.

$R^8$ is even more preferably
(i) phenyl which is unsubstituted or substituted by halogen, $C_1$-$C_2$-alkyl or $C_1$-$C_2$-alkoxy;
(ii) 2-furanyl, 2-thiazoyl, 2- 3- or 4-pyridyl or 4- or 5-pyrimidinyl, each unsubstituted or substituted by $C_1$-$C_2$-alkyl, $C_1$-$C_2$-haloalkyl and $C_1$-$C_4$-alkoxycarbonyl;
(iii) oxetan-3-yl, thietan-3-yl, thietan-3-yl-1-oxide, thietan-3-yl-1,1-dioxide, or tetrahydrofuran-2- or -3-yl;
(iv) $C_1$-$C_2$-alkyl which is unsubstituted or substituted by chlorine; fluorine; $C_1$-$C_2$-alkoxy; —C(O)NHR$^{10}$ wherein R$^{10}$ is $C_1$-$C_4$-alkyl, 2,2,2-trifluoroethyl, cyanomethyl, propargyl or cyclopropylmethyl; 2-furanyl; 2-thiazoyl; 2- 3- or 4-pyridyl; 4- or 5-pyrimidinyl; oxetan-3-yl; thietan-3-yl; thietan-3-yl-1-oxide; thietan-3-yl-1,1-dioxide; tetrahydrofuran-2-yl; tetrahydrofuran-3-yl; or phenyl which is unsubstituted or substituted by halogen, $C_1$-$C_2$-alkyl or $C_1$-$C_2$-alkoxy;
(v) allyl; (vi) propargyl; (vii) $C_3$-$C_4$-cycloalkyl; or (viii) $C_3$-$C_4$-cycloalkylmethyl.

$R^{11}$ is preferably H. $R^{12}$ and $R^{13}$ are each independently preferably $C_1$-$C_2$-alkyl, in particular each methyl. According to one embodiment $R^7$ and $R^8$ together are a group =CH—N(CH$_3$)$_2$ or =CH—C(NH$_2$)—OCH$_3$.

According to a further embodiment $R^7$ and $R^8$ together with the N-atom to which they are attached, form a morpholinyl ring, a piperidinyl ring or a 1-piperazinyl ring which is unsubstituted in the 4-position or substituted by $C_1$-$C_2$-alkyl, N,N-di-$C_1$-$C_2$-alkylaminomethyl or N,N-di-$C_1$-$C_2$-alkylaminocarbonylmethyl.

W and W' are each independently preferably O.

A preferred embodiment of the invention concerns a compound of formula

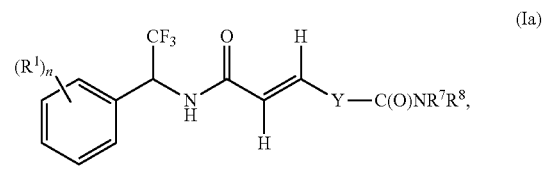

wherein $R^1$, $R^7$, $R^8$, Y and n are as defined above including the preferences.

A further preferred embodiment concerns a compound of the formula (Ia) above, wherein $R^1$ is halogen, cyano, nitro, $C_1$-$C_2$-alkyl, $C_1$-$C_2$-haloalkyl, $C_1$-$C_2$-haloalkylthio, $C_1$-$C_2$-alkoxy, $C_1$-$C_2$ haloalkoxy or $C_1$-$C_2$-alkylsulfonyl, n is 1 or 2; $R^7$ is H or $C_1$-$C_2$-alkyl, and $R^8$ is (i) phenyl, which is unsubstituted or substituted by 1 or 2, same or different substituents selected from the group consisting of halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, cyano, nitro, aminocarbonyl and unsubstituted or halogen-, $C_1$-$C_2$-alkyl-, $C_1$-$C_2$-haloalkyl-, $C_1$-$C_2$-alkoxy-, $C_1$-$C_2$-haloalkoxy-, cyano- or nitro-substituted phenyl and phenoxy; or is (ii) 2- or 3-furanyl, 2- or 3-thienyl, 1-, 2- or 3-pyrrolyl, 1-, 2-, 4- or 5-imidazolyl, 1- or 4-pyrazolyl, 2-, 4- or 5-thiazolyl, 1,2,4-triazol-3- or -4-yl, 1,2,3-triazin-1- or 2-yl, 2- 3- or 4-pyridyl or 4- or 5-pyrimidinyl, which is each unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano, nitro, aminocarbonyl or $C_1$-$C_4$-alkoxycarbonyl; or is (iii) oxetanyl, thietanyl, thietanyl-1 oxide, thietanyl-1,1-dioxide, tetrahydrofuranyl, tetrahydrothiophenyl, pyrrolidinyl, 2- or 3-pyrrolidonyl, 1,3-dioxolanyl, 1,2- or 1,3-oxazolidinyl, tetrahydropyranyl, piperidinyl, tetrahydrothiopyranyl, tetrahydrothiopyranyl-1,1-dioxid, morpholinyl, or 1,3- or 1,4-dioxanyl, which is each unsubstituted or substituted by halogen, cyclopropyl, $C_1$-$C_2$-haloalkyl, $C_1$-$C_2$-alkoxy, $C_1$-$C_2$-haloalkoxy, cyano, nitro, or $C_1$-$C_4$-alkoxycarbonyl; or is (iv) $C_1$-$C_2$-alkyl which is unsubstituted or substituted by halogen; $C_1$-$C_2$-alkoxy; carboxy; $C_1$-$C_2$-alkoxycarbonyl; a radical —C(O)NHR$^{10}$ wherein R$^{10}$ is $C_1$-$C_4$-alkyl, halo-$C_1$-$C_2$-alkyl, cyano-$C_1$-$C_2$-alkyl, $C_2$-$C_3$-alkynyl or cyclopropylmethyl; phenyl which is unsubstituted or substituted by halogen, $C_1$-$C_2$-alkyl or $C_1$-$C_2$-alkoxy; or a heterocyclic ring selected from 2- or 3-furanyl, 2- or 3-thienyl, 1-, 2- or 3-pyrrolyl, 1-, 2-, 4- or 5-imidazolyl, 1- or 4-pyrazolyl, 2-, 4- or 5-thiazolyl, 1,2,4-triazol-3- or -4-yl, 1,2,3-triazin-1- or 2-yl, 2- 3- or 4-pyridyl, 4- or 5-pyrimidinyl, oxetanyl, thietanyl, thietanyl-1-oxide, thietanyl-1,1-dioxide and tetrahydrofuranyl, which is each unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano, nitro, aminocarbonyl or $C_1$-$C_4$-alkoxycarbonyl; or is (v) $C_2$-$C_4$-alkenyl; (vi) $C_2$-$C_4$-alkynyl; (vii) $C_3$-$C_6$-cycloalkyl; or (viii) $C_3$-$C_6$-cycloalkylmethyl.

Still a further preferred embodiment concerns a compound of the formula (Ia) above, wherein halogen or CF$_3$, n is 1 or 2; $R^7$ is H, and $R^8$ is (i) phenyl which is unsubstituted or substituted by halogen, $C_1$-$C_2$-alkyl or $C_1$-$C_2$-alkoxy;

(ii) 2-furanyl, 2-thiazoyl, 2- 3- or 4-pyridyl or 4- or 5-pyrimidinyl, each unsubstituted or substituted by $C_1$-$C_2$-alkyl, $C_1$-$C_2$-haloalkyl and $C_1$-$C_4$-alkoxycarbonyl;

(iii) oxetan-3-yl, thietan-3-yl, thietan-3-yl-1-oxide, thietan-3-yl-1,1-dioxide, or tetrahydrofuran-2- or -3-yl;

(iv) $C_1$-$C_2$-alkyl which is unsubstituted or substituted by chlorine; fluorine; $C_1$-$C_2$-alkoxy; —C(O)NHR$^{10}$ wherein R$^{10}$ is $C_1$-$C_4$-alkyl, 2,2,2-trifluoroethyl, cyanomethyl, propargyl or cyclopropylmethyl; 2-furanyl; 2-thiazoyl; 2- 3- or 4-pyridyl; 4- or 5-pyrimidinyl; oxetan-3-yl; thietan-3-yl; thietan-3-yl-1-oxide; thietan-3-yl-1,1-dioxide; tetrahydrofuran-2-yl; tetrahydrofuran-3-yl; or phenyl which is unsubstituted or substituted by halogen, $C_1$-$C_2$-alkyl or $C_1$-$C_2$-alkoxy;

(v) allyl; (vi) propargyl; (vii) $C_3$-$C_4$-cycloalkyl; or (viii) $C_3$-$C_4$-cycloalkylmethyl.

Still a further preferred embodiment concerns a compound of formula

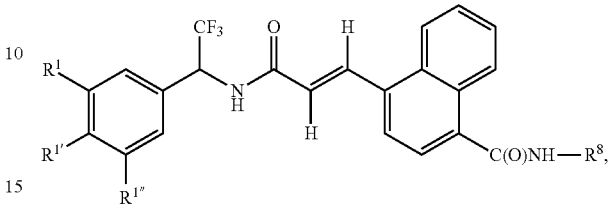

(Ib)

wherein $R^1$ is halogen, CF$_3$ or OCF$_3$; $R^{1'}$ and $R^{1'''}$ are each independently H or halogen; and $R^8$ is as defined before including the above-given preferences. In particular, a compound of formula (Ib) is preferred, wherein $R^8$ is (i) $C_1$-$C_3$-alkyl which is unsubstituted or substituted by fluorine or cyano;

(ii) $C_3$-$C_4$-cycloalkyl, which is unsubstituted or substituted by methyl, halogen or cyano;

(iii) 2-furanyl;

(iv) thietan-4-yl or thietan-3-yl-methyl; or (v) a radical

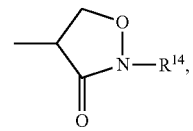

wherein $R^{14}$ is $C_1$-$C_2$-alkyl or halo-$C_1$-$C_2$-alkyl.

A especially preferred compound according to the invention is a compound of the above-given formula (Ib), wherein $R^1$ is CF$_3$, $R^{1'}$ and $R^{1'''}$ are each H or halogen, in particular each H, and for $R^8$, the above-given meanings and preferences apply.

The compounds of this invention can exist as one or more stereoisomers. The various stereoisomers include enantiomers, diastereomers, atropisomers and geometric isomers. In case the compounds of the formula (I), (Ia) or (Ib) have a chiral carbon atom, they may have either an (R) or an (S) configuration. The present invention encompasses compounds formula (I), (Ia) or (Ib) both with (S) and with (R) configuration at the particular chiral carbon atoms, which means that the present invention covers the compounds of the general formula (I), (Ia) and (Ib) in which the carbon atoms in question each independently have an (R) configuration; or have an (S) configuration.

If a plurality of chiral centres are present in the compounds of the formula (I), (Ia) or (Ib), any desired combinations of the configurations of the chiral centres are possible, which means that (1) one chiral centre may have (R) configuration and the other chiral centre (S) configuration; (2) one chiral centre may have (R) configuration and the other chiral centre (R) configuration; and (3) one chiral centre may have (S) configuration and the other chiral centre (S) configuration.

One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers, or as an optically active form.

One skilled in the art will appreciate that not all nitrogen containing heterocyclic rings can form N-oxides since the nitrogen requires an available lone pair for oxidation to the oxide; one skilled in the art will recognize those nitrogen containing heterocyclic rings which can form N-oxides. One skilled in the art will also recognize that tertiary amines can form N-oxides. Synthetic methods for the preparation of N-oxides of heterocyclic rings and tertiary amines are very well known by one skilled in the art including the oxidation of heterocyclic rings and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyl dioxirane These methods for the preparation of N-oxides have been extensively described and reviewed in the literature. The manufacture of suitable S-oxides may be performed in an analogous manner using, for example, the same kind of oxidants as mentioned above for the N-oxides.

One skilled in the art recognizes that because of the environment and under physiological conditions salts of chemical compounds are in equilibrium with their corresponding nonsalt forms, salts share the biological utility of the nonsalt forms. Thus a wide variety of salts of the compounds of formula (I) are useful for control of invertebrate pests (i.e. are veterinarily or agriculturally suitable). The salts of the compounds of formula (I) include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of formula (I) contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from formula (I), N-oxides and veterinary acceptable and agriculturally suitable salts thereof. The compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. Exemplary prodrugs are, e.g., esters of free carboxylic acids and S-acyl and O-acyl derivatives of thiols, alcohols or phenols, wherein acyl has a meaning as defined herein. Preferred are veterinary or pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde. Moreover, drugs containing an acidic NH group, such as imidazole, imide, indole and the like, have been masked with N-acyloxymethyl groups. Hydroxy groups have been masked as esters and ethers. EP0 039 051 discloses Mannich-base hydroxamic acid prodrugs, their preparation and use. In view of the close relationship between the compounds, the compounds in the form of their salts and the pro-drugs, any reference to the compounds of the present invention is to be understood as referring also to the corresponding pro-drugs of the compounds of the present invention, as appropriate and expedient.

The compounds of formula (I), (Ia) or (Ib), wherein W is O, may be prepared, for example, by reacting an amine of formula

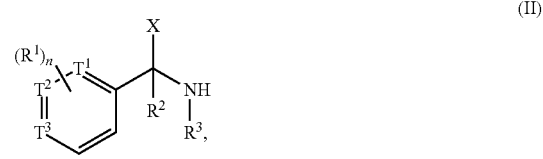

with a carboxylic acid or a derivative thereof of formula

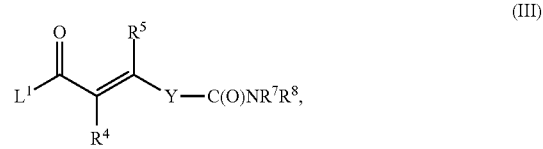

wherein $R^1$-$R^5$, $R^6$, $R^7$, $T^1$-$T^3$, Y and n are each as defined above and $L^1$ is, for example OH or halogen.

Concerning the compound of formula (III), it is possible to use an acid halide (e.g. $L^1$=chlorine) in the presence of a base, for example triethylamine or sodium hydroxide. In the alternative, the carboxylic acid ($L^1$=OH) can also be employed, in the presence of a coupling reagent, for example dicyclohexylcarbodiimide, and/or additives such as 1-hydroxybenzotriazole. Further suitable coupling reagents are 1-ethyl-3-(3-dimethylamino-propyl)carbodiimide, 1,1'-carbonyl-1H-imidazole or similar compounds. The coupling reagent employed to perform the preparation process may be all those suitable for preparing an ester or amide bond as known from textbooks or organic chemistry. In addition, it is also possible to use mixed anhydrides for the preparation of a compound of formula (I). In this process, it is possible to use different chloroformic esters, for example isobutyl chloroformate, isopropyl chloroformate. It is likewise possible for this purpose to use diethylacetyl chloride, trimethylacetyl chloride and the like.

The compounds of formula (I) in which W is O (oxygen atom) may subsequently be reacted with a thionating reagent to obtain compounds of formula (I) in which W is S (sulphur atom).

An alternative process for preparing the compounds of formula (I) or (Ia) comprises reacting first of all an amine compound of the above given formula (II) with an acrylic acid derivative of formula

wherein L¹ is as defined above, and reacting the resulting acrylamide of formula $$(R^1)_n\text{-}T^2\text{=}T^1\text{-}C(X)(R^2)\text{-}N(R^3)\text{-}C(O)\text{-}CH\text{=}CH_2 \quad (V)$$

further with a compound of formula $$L^2\text{-}Y\text{-}C(O)NR^7R^8 \quad (VI),$$

wherein Y, R⁷ and R⁸ are as defined and L² is, for example, chlorine, bromine, iodine or triflate, in the presence of a palladium catalyst to obtain compounds of the general formula (I), wherein W is O.

Suitable reaction conditions for the first step, the amide formation, correspond to the reaction conditions specified for the reactions of carboxylic acid derivatives of the formula (III) with amines of the formula (II) above.

Acrylamides of the formula (V) can subsequently be reacted with halogen compounds of the formula (VI) by literature methods in a palladium-catalyzed reaction to give the inventive compounds of the formula (I). The palladium catalyst used may, for example, be palladium acetate in the presence of triphenylphosphine.

Compounds of the formula (I) can also be obtained by converting functional groups from other compounds of the formula (I) by methods known from textbooks of organic chemistry.

The precursor compounds of formulae (II) and (IV) are known and/or commercially available or can be obtained by methods known in the art.

Carboxylic acids of formula (III) where L¹ is OH can be synthesized by methods known from the literature. For example, an acid derivatives of the above formula (III) may be obtained by a Heck reaction proceeding from a (het)aryl compound of formula (VI) as mentioned above by reaction with 1-propenoic acid derivatives in the presence of a multitude of palladium catalysts, for example palladium acetate. It is also possible in the same way to use commonly known anilines, which are first converted to the diazonium salt in the presence of a diazotizing reagent, for example sodium nitrite, and then reacted with 1-propenoic acid derivatives in the presence of a palladium catalyst, for example palladium acetate.

The compounds of formula (VI) may be obtained from the corresponding carboxylic acids of formula $$L^2\text{-}Y\text{-}C(O)OH \quad (VII)$$

by reaction with an amine of formula $$HNR^7R^8 \quad (VIII)$$

in a manner known per se.

The acids of the formula (III) can also be obtained by reaction of aromatic aldehydes with malonic acid. For example, the aldehyde functional group of a compound of formula $$H\text{-}C(O)\text{-}Y\text{-}L^3, \quad (IX)$$

wherein Y is as described above and L³ is a leaving group, in particular fluorine, chlorine or bromine, is first of all protected, for example, by converting it to a cyclic acetal, then a suitable side chain —C(O)NR⁷R⁸ is introduced by replacing L³ by methods known from textbooks of organic chemistry. Following deprotecting of the aldehyde, the resulting compound of formula $$H\text{-}C(O)\text{-}Y\text{-}C(O)NR^7R^8, \quad (X)$$

can subsequently be reacted, in analogy to literature methods, with malonic acid in the presence of a nitrogen base, for example piperidine, with decarboxylation to give a compound of formula (III).

The working examples provide further details concerning the synthesis of the compounds of the present invention.

The compounds of the formula (I) according to the invention are notable for their broad activity spectrum and are valuable active ingredients for use in pest control. They are particularly suitable in the control of ectoparasites and to a certain extent also for controlling endoparasites on and in animals and in the hygiene field, whilst being well tolerated by vertebrates such as warm-blooded animals and fishes.

Animals in the context of the invention are understood to include vertebrates. The term vertebrate in this context is understood to comprise, for example fishes, amphibians, reptiles, birds, and mammals including humans. One preferred group of vertebrates according to the invention comprises warm-blooded animals including farm animals, such as cattle, horses, pigs, sheep and goats, poultry such as chickens, turkeys, guinea fowls and geese, fur-bearing animals such as mink, foxes, chinchillas, rabbits and the like, as well as companion animals such as ferrets, guinea pigs, rats, hamster, cats and dogs, and also humans. A further group of preferred vertebrates according to the invention comprises fishes including salmons.

In the context of the present invention, ectoparasites are understood to be in particular insects, acari (mites and ticks), and crustaceans (sea lice). These include insects of the following orders: Lepidoptera, Coleoptera, Homoptera, Hemiptera, Heteroptera, Diptera, Dictyoptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Lucilia sericata, Hypoderma bovis, Hypoderma lineatum, Chrysomyia chloropyga, Dermatobia hominis, Cochliomyia hominivorax, Gasterophilus intestinalis, Oestrus ovis*, biting flies such as *Haematobia irritans irritans, Haematobia irritans exigua, Stomoxys calcitrans*, horse-flies (Tabanids) with the subfamilies of Tabanidae such as *Haematopota* spp. (e.g. *Haematopota pluvialis*) and *Tabanus* spp, (e.g. *Tabanus nigrovittatus*) and Chrysopsinae such as *Chrysops* spp. (e.g. *Chrysops caecutiens*); Hippoboscids such as *Melophagus ovinus* (sheep ked); tsetse flies, such as *Glossinia* spp.; other biting insects like midges, such as Ceratopogonidae (biting midges), Simuliidae (Blackflies), Psychodidae (Sandflies); but also blood-sucking insects, for example mosquitoes, such as *Anopheles* spp, *Aedes* spp and *Culex* spp, fleas, such as

*Ctenocephalides felis* and *Ctenocephalides canis* (cat and dog fleas), *Xenopsylla cheopis, Pulex irritans, Ceratophyllus gallinae, Dermatophilus penetrans*, blood-sucking lice (Anoplura) such as *Linognathus* spp, *Haematopinus* spp, *Solenopotes* spp, *Pediculus humanis*; but also chewing lice (Mallophaga) such as *Bovicola (Damalinia) ovis, Bovicola (Damalinia) bovis* and other *Bovicola* spp. Ectoparasites also include members of the order Acarina, such as mites (e.g. *Chorioptes bovis, Cheyletiella* spp., *Dermanyssus gallinae, Ortnithonyssus* spp., *Demodex canis, Sarcoptes scabiei, Psoroptes ovis* and *Psorergates* spp. and ticks. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest vertebrates, for example warm-blooded animals including farm animals, such as cattle, horses, pigs, sheep and goats, poultry such as chickens, turkeys, guinea-fowls and geese, fur-bearing animals such as mink, foxes, chinchillas, rabbits and the like, as well as companion animals such as ferrets, guinea pigs, rats, hamster, cats and dogs, but also humans and fishes.

The compounds of the formula (I) according to the invention are also active against all or individual development stages of animal pests showing normal sensitivity, as well as those showing resistance to widely used parasiticides. This is especially true for resistant insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds of the formula (I) can also be used against hygiene pests, especially of the order Diptera of the families Muscidae, Sarcophagidae, Anophilidae and Culicidae; the orders Orthoptera, Dictyoptera (e.g. the family Blattidae (cockroaches), such as *Blatella germanica, Blatta orientalis, Periplaneta americana*) and Hymenoptera (e.g. the families Formicidae (ants) and Vespidae (wasps).

Surprisingly, the compounds of formula (I) are also effective against ectoparasites of fishes, specially the sub-class of Copepod, e.g. order of Siphonostomatoida, in particular sea lice, whilst being well tolerated by fish.

The compounds of formula (I) can also be used against hygiene pests, especially of the order Diptera of the families Sarcophagidae, Anophilidae and Culicidae; the orders Orthoptera, Dictyoptera (e.g. the family Blattidae) and Hymenoptera (e.g. the family Formicidae).

Compounds of the formula (I) also have sustainable efficacy on parasitic mites and insects of plants. In the case of spider mites of the order Acarina, they are effective against eggs, nymphs and adults of *Tetranychidae* (*Tetranychus* spp. and *Panonychus* spp.).

They have high activity against sucking insects of the order Homoptera, especially against pests of the families Aphididae, Delphacidae, Cicadellidae, Psyllidae, Loccidae, Diaspididae and Eriophydidae (e.g. rust mite on citrus fruits); the orders Hemiptera, Heteroptera and Thysanoptera, and on the plant-eating insects of the orders Lepidoptera, Coleoptera, Diptera and Orthoptera They are similarly suitable as a soil insecticide against pests in the soil.

The compounds of formula (I) are therefore effective against all stages of development of sucking insects and eating insects on crops such as cereals, cotton, rice, maize, soya, potatoes, vegetables, fruit, tobacco, hops, citrus, avocados and other crops.

The compounds of formula I are also effective against plant nematodes of the species *Meloidogyne, Heterodera, Pratylenchus, Ditylenchus, Radopholus, Rizoglyphus* etc.

Certain compounds of the formula (I) seem to be also effective against certain species of helminths. Helminths are commercially important because they cause serious diseases in mammals and poultry, e.g. in sheep, pigs, goats, cattle, horses, donkeys, camels, dogs, cats, rabbits, guinea-pigs, hamsters, chicken, turkeys, guinea fowls and other farmed birds, as well as exotic birds. Typical nematodes are: *Haemonchus, Trichostrongylus, Ostertagia, Nematodirus, Cooperia, Ascaris, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris, Parascaris* and *Dirofilaria*. The trematodes include, in particular, the family of Fasciolideae, especially *Fasciola hepatica*.

The good pesticidal activity of the compounds of formula (I) according to the invention corresponds to a mortality rate of at least 50-60% of the pests mentioned, more preferably to a mortality rate over 90%, most preferably to 95-100%. The compounds of formula (I) are preferably employed internally and externally in unmodified form or preferably together with the adjuvants conventionally used in the art of formulation and may therefore be processed in a known manner to give, for example, liquid formulations (e.g. spot-on, pour-on, spray-on, emulsions, suspensions, solutions, emulsifiable concentrates, solution concentrates), semi-solid formulations (e.g. creams, ointments, pastes, gels, liposomal preparations) and solid preparations (e.g. food additives tablets including e. g. capsules, powders including soluble powders, granules, or embeddings of the active ingredient in polymeric substances, like implants and microparticles). As with the compositions, the methods of application are selected in accordance with the intended objectives and the prevailing circumstances. The formulation, i.e. preparations containing the active ingredient of formula (I), or combinations of these active ingredients with other active ingredients, and optionally a solid, semi-solid or liquid adjuvant, are produced in a manner known per se, for example by intimately mixing, kneading or dispersing the active ingredients with compositions of excipients, whereby the physiological compatibility of the formulation excipients must be taken into consideration.

The solvents in question may be: alcohols (aliphatic and aromatic), such as benzylalcohol, ethanol, propanol, isopropanol or butanol, fatty alcohols, such as oleyl alcohol and glycols and their ethers and esters, such as glycerin, propylene glycol, dipropylene glycol ether, ethylene glycol, ethylene glycol monomethyl or -ethyl ether and butyl dioxytol, carbonates, such as propylene carbonate, ketones, such as cyclohexanone, isophorone or diacetanol alcohol and polyethylene glycols, such as PEG 300. In addition, the compositions may comprise strong polar solvents, such as N-methyl-2-pyrrolidone, dimethyl sulfoxide or dimethylformamide, or water, fatty acid esters, such as ethyl oleate or isopropylpalmitate, vegetable oils, such as rape, castor, coconut, or soybean oil, synthetic mono-, di-, triglycerides like e.g. glyceryl monostearate and medium chain triglycerides and also, if appropriate, silicone oils. The mentioned ingredients may also serve as carrier for particulate application froms.

As ointment base resp. structure building ingredients the following excipients may be used: Petroleum based substances, such as Vaseline or paraffines, bases made from wool fat, like e.g. lanolin or lanolin alcohols, polyethylene glycols like e.g. macrogols and lipid bases like e.g. phospholipids or triglycerids, such as hydrogenated vegetable oils.

The use of emulsifiers, wetting agents and spreading agents may also be required, in general, lecithins like soy lecithin, salts of fatty acids with alkaline earth and alkali metals, alkyl sulfates like sodium cetylstearyl sulphate, cholates, fatty alcohols like cetyl alcohol, sterols like cholestesterol, polyoxyethylene sorbitan fatty acid esters like polysorbate 20, sorbitan fatty acid esters like sorbitan mono laureate, fatty acid esters and fatty alcohol ethers of polyoxyethylene like poloxyl oleyl ether, polyoxypropylene polyoxyethylene block copolymers as e.g. Pluronic™, saccharose esters like saccharose distearate, polyglyceryl fatty acid esters like polyglycerol oleate and fatty acid esters like e.g. ethyl oleate or isopropylmyristate.

The formulations may also include gelifying and stiffening agents, like e.g. polyacrylic acid derivatives, cellulose ethers, polyvinyl alcohols, polyvinylpyrrolidons and fine disperse silicium dioxide.

As polymeric agents with controlled release properties, may be applied derivatives made by e.g. polylactic acid, polylactic coglycolic acid, poly orthoester, polyethylene carbonate, poly anhydrids and starch and PVC based matrices.

The addition of penetration enhancers like ketones, sulfoxides, amides, fatty acid esters and fatty alcohols may be necessary.

Also preservatives like sorbic acid, benzyl alcohol and parabenes, and antioxidants as e.g. alpha tocopherol may be added.

The active ingredient or combinations of the active ingredient may also applied in capsules, like hard gelatine capsules or soft capsules.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), lubricants (e.g. magnesium stearate), glidants (e.g. colloidal silicon dioxide) and disintegrants (e.g. cellulose derivatives) and acid resistant coatings, like e.g. acrylic acid esters.

The compounds of formula (I) according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. For example, in case of a compound of formula (I) having a particular efficacy as adulticide, i.e. since it is effective in particular against the adult stage of the target parasites, the addition of a pesticide which instead attack the juvenile stages of the parasites may be very advantageous, or vice versa. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula (I).

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broadband acaricides and nematicides; and also the well known anthelminthics and insect- and/or acarid-deterring substances, said repellents or detachers. Non-limitative examples of suitable insecticides and acaricides are mentioned in WO 2009/071500, compounds Nos. 1-284 on pages 18-21. Non-limitative examples of suitable anthelminthics are mentioned in WO 2009/071500, compounds (A1)-(A31) on page 21. Non-limitative examples of suitable repellents and detachers are mentioned in WO 2009/071500, compounds (R1)-(R3) on page 21 and 22. Non-limitative examples of suitable synergists are mentioned in WO 2009/071500, compounds (S1)-(S3) on page 22. The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature.

As a consequence of the above details, a further aspect of the present invention relates to a combination preparation for the control of parasites on vertebrates, in particular on warm-blooded animals or on fishes, characterised in that it contains, in addition to a compound of formula (I), at least one further active ingredient having the same or different sphere of activity and at least one physiologically acceptable carrier. The present invention is not restricted to two-fold combinations.

As a rule, the insecticidal and acaricidal compositions according to the invention contain 0.1 to 99% by weight, especially 0.1 to 95% by weight of one or more active ingredients of formula (I), 99.9 to 1% by weight, especially 99.8 to 5% by weight of a solid or liquid admixture, including 0 to 25% by weight, especially 0.1 to 25% by weight of a surfactant. Application of the compositions according to the invention to the animals to be treated may take place topically, perorally, parenterally or subcutaneously, the composition being present, for example, in the form of solutions, emulsions, suspensions, (drenches), powders, tablets, boli, capsules, chewable treats, collars, eartags and pour-on formulations. Preferred topical formulations are understood to refer to a ready-to-use solution in form of a spot-on, pour-on or spray-on formulation often consisting of a dispersion or suspoemulsion or a combination of active ingredient and spreading auxiliaries. The expression spot-on or pour-on method is understood to refer to a ready-to-use concentrate intended to be applied topically and locally on the animal. This sort of formulation is intended to be applied directly to a relatively small area of the animal, preferably on the animal's back and breech or at one or several points along the line of the back and breech. It is applied as a low volume of about 0.05 to 1 ml per kg, preferably about 0.1 ml per kg, with a total volume from 0.1 to 100 ml per animal, preferably limited to a maximum of about 50 ml. However, it goes without saying that the total volume has to be adapted to the animal that is in need of the treatment and will clearly be different, for example, in young cats and in cattle. These pour-on and spot-on formulations are designed to spread all around the animal giving protection or treatment to almost any part of the animal. Even so the administration is carried out by applying a swab or spray of the pour-on or spot-on formulation to a relatively small area of the coat, one observes that from the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 98.9% by weight of a compound of formula (I), 0.1 to 80% by weight of dispersing agent and 1 to 98.9% by weight of solvent. The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

Whereas it is preferred to formulate commercial products as concentrates, the end user will often use dilute formulations. However, this depends on the mode of administration. Orally administered products are most often used in diluted form or as feed additives, whereas commercial pour-on and spot-on formulations are normally ready-to-use concentrates. Such compositions may also contain further additives, such as stabilisers, anti-foaming agents, viscosity regulators, binding agents or tackifiers, as well as other active ingredients, in order to achieve special effects.

Insecticidal and acaricidal compositions of this type, which are used by the end user, similarly form a constituent of the present invention.

In each of the processes according to the invention for pest control or in each of the pest control compositions according to the invention, the active ingredients of formula (I) can be used in all of their steric configurations or in mixtures thereof.

The invention also includes a method of prophylactically protecting animals, especially productive livestock, domestic animals and pets, against parasitic helminths, which is characterised in that the active ingredients of formula (I) or the active ingredient formulations prepared therefrom are administered to the animals as an additive to the feed, or to the drinks or also in solid or liquid form, orally or by injection or parenterally. The invention also includes the compounds of formula (I) according to the invention for usage in one of the said processes.

The following examples serve merely to illustrate the invention without restricting it, the term active ingredient representing any substance as described in the preparation examples. In particular, preferred formulations are made up as follows:
(%=percent by weight)
Formulation Examples
1. Granulate

|  |  | a) | b) |
|---|---|---|---|
| (i) | active ingredient | 5% | 10% |
|  | kaolin | 94% | — |
|  | highly dispersed silicic acid | 1% | — |
|  | attapulgite | — | 90% |

The active ingredient is dissolved in methylene chloride, sprayed onto the carrier and the solvent subsequently concentrated by evaporation under vacuum. Granulates of this kind can be mixed with the animal feed.

| (ii) | active ingredient | 3% |
|---|---|---|
|  | polyethylene glycol (mw 200) | 3% |
|  | kaolin | 94% |

(mw = molecular weight)

The finely ground active ingredient is evenly applied in a mixer to the kaolin which has been moistened with polyethylene glycol. In this way, dust-free coated granules are obtained.

2. Tablets or Boli

| I | active ingredient | 33.00% |
|---|---|---|
|  | methylcellulose | 0.80% |
|  | silicic acid, highly dispersed | 0.80% |
|  | corn starch | 8.40% |
| II | lactose, cryst. | 22.50% |
|  | corn starch | 17.00% |
|  | microcryst. cellulose | 16.50% |
|  | magnesium stearate | 1.00% |

I Methyl cellulose is stirred into water. After the material has swollen, silicic acid is stirred in and the mixture homogeneously suspended. The active ingredient and the corn starch are mixed. The aqueous suspension is worked into this mixture and kneaded to a dough. The resulting mass is granulated through a 12 M sieve and dried.
II All 4 excipients are mixed thoroughly.
III The preliminary mixes obtained according to I and II are mixed and pressed into tablets or boli.
3. Injectables
A. Oily vehicle (slow release)

| (i) | active ingredient | 0.1-1.0 g |
|---|---|---|
|  | groundnut oil | ad 100 ml |
| (ii) | active ingredient | 0.1-1.0 g |
|  | sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 µm.

B Water-Miscible Solvent (Average Rate of Release)

| (i) | active ingredient | 0.1-1.0 g |
|---|---|---|
|  | 4-hydroxymethyl-1,3-dioxolane (glycerol formal) | 40 g |
|  | 1,2-propanediol | ad 100 ml |
| (ii) | active ingredient | 0.1-1.0 g |
|  | glycerol dimethyl ketal | 40 g |
|  | 1,2-propanediol | ad 100 ml |

Preparation: The active ingredient is dissolved in part of the solvent whilst stirring, made up to the desired volume and sterile-filtered through a suitable membrane filter with a pore size of 0.22 µm.

C. Aqueous Solubilisate (Rapid Release)

| (i) | active ingredient | 0.1-1.0 g |
|---|---|---|
|  | polyethoxylated castor oil (40 ethylene oxide units) | 10 g |
|  | 1,2-propanediol | 20 g |
|  | benzyl alcohol | 1 g |
|  | aqua ad inject. | ad 100 ml |
| (ii) | active ingredient | 0.1-1.0 g |
|  | polyethoxylated sorbitan monooleate (20 ethylene oxide units) | 8 g |
|  | 4-hydroxymethyl-1,3-dioxolane (glycerol formal) | 20 g |
|  | benzyl alcohol | 1 g |
|  | aqua ad inject. | ad 100 ml |

Preparation: The active ingredient is dissolved in the solvents and the surfactant, and made up with water to the desired volume. Sterile filtration through an appropriate membrane filter of 0.22 µm pore size.

4. Pour on

| (i) | active ingredient | 5 g |
|---|---|---|
|  | isopropyl myristate | 10 g |
|  | isopropanol | ad 100 ml |
| (ii) | active ingredient | 2 g |
|  | hexyl laurate | 5 g |
|  | medium-chained triglyceride | 15 g |
|  | ethanol | ad 100 ml |
| (iii) | active ingredient | 2 g |
|  | oleyl oleate | 5 g |
|  | N-methyl-pyrrolidone | 40 g |
|  | isopropanol | ad 100 ml |

5. Spot on

| (i) | active ingredient | 0-15 g |
|---|---|---|
|  | diethyleneglycol monoethylether | ad 100 ml |
| (ii) | active ingredient | 10-15 g |
|  | octyl palmitate | 10 g |
|  | isopropanol | ad 100 ml |
| (iii) | active ingredient | 10-15 g |
|  | isopropanol | 20 g |
|  | benzyl alcohol | ad 100 ml |

6. Spray on

| (i) | active ingredient | 1 g |
|---|---|---|
|  | isopropanol | 40 g |
|  | propylene carbonate | ad 100 ml |
| (ii) | active ingredient | 1 g |
|  | propylene glycol | 10 g |
|  | isopropanol | ad 100 ml |

The aqueous systems may also preferably be used for oral and/or intraruminal application. The compositions may also contain further additives, such as stabilisers, e.g. where appropriate epoxidised vegetable oils (epoxidised coconut oil, rapeseed oil, or soybean oil); antifoams, e.g. silicone oil, preservatives, viscosity regulators, binders, tackifiers, as well as fertilisers or other active ingredients to achieve special effects.

Further biologically active substances or additives, which are neutral towards the compounds of formula (I) and do not have a harmful effect on the host animal to be treated, as well as mineral salts or vitamins, may also be added to the described compositions.

The following examples serve to illustrate the invention. The letter 'h' stands for hour. The starting materials are known and partially commercially available or may be produced in analogy to methods known per se.

Analysis of the purified samples is in each case done using a Waters Autopurification (HPLC/MS) system with a reversed phase column using method B described below. The samples are characterized by m/z and retention time. The above-given retention times relate in each case to the use of a solvent system comprising two different solvents, solvent A: $H_2O+0.01\%$ HCOOH, and solvent B: $CH_3CN+0.01\%$ HCOOH).

Method B: column Waters XTerra MS C18 5 µm, 50×4.6 mm (Waters), flow rate of 3.00 mL/min with a time-dependent gradient as given in the Table:

| Time [min] | A [%] | B [%] |
|---|---|---|
| 0 | 90 | 10 |
| 0.5 | 90 | 10 |
| 2.5 | 5 | 95 |
| 2.8 | 5 | 95 |
| 2.9 | 90 | 10 |
| 3.0 | 90 | 10 |

EXAMPLE 1

This example illustrates the preparation of N-(cyclopropylmethyl)-4-[(1E)-2-({2,2,2-trifluoro-1-[3-(trifluoromethyl)phenyl]ethyl}carbamoyl)eth-1-en-1-yl]naphthalene-1-carboxamide (Compound 1.1 in Table 1)

Step A:

Lithium bis(trimethylsilyl)amide (LiHMDS, 1M in THF, 8.3 mL) was added dropwise at room temperature to a solution of 2,2,2-trifluoro-3-(trifluoromethyl)-acetophenone (2.0 g) in dry toluene (20 mL). The reaction mixture was stirred at RT for 2 hours. $BH_3$ (1M in THF, 16.6 mL) was then added and the reaction mixture was stirred at RT for another 2 hours. The reaction mixture was cooled down to 0° C. and a solution of 2M NaOH (10 mL) was added dropwise (warning: exothermic reaction). After 1 hour, the mixture was diluted with ethyl acetate, water was added, and the organic layer was extracted. Organic layer was washed with water, dried over magnesium sulfate and concentrated in vacuo to afford 2,2,2-Trifluoro-1-(3-trifluoromethyl-phenyl)-ethylamine (1.9 g) as yellow oil.

Step B:

Acryloyl chloride (650 µL) was added dropwise to a solution of 2,2,2-Trifluoro-1-(3-trifluoromethyl-phenyl)- ethylamine (2.0 g) and pyridine (800 μL) in dry dichloromethane at 0° C. The reaction mixture was stirred at room temperature for 5 hours. After evaporation of the solvents, the residue was purified by automatic flash chromatography on silica gel (cyclohexane/EtOAc) to yield N-[2,2,2-Trifluoro-1-(3-trifluoromethyl-phenyl)-ethyl]acrylamide (1.0 g) as white solid.

Step C:

A mixture of N-[2,2,2-Trifluoro-1-(3-trifluoromethyl-phenyl)-ethyl]-acrylamide (2.1 g), 4-bromo-naphtalene-carboxylic acid (1.7 g), triphenylphosphine (363 mg) and triethylamine (8.5 mL) in dry N,N-dimethylformamide (28 mL) was degassed under argon in a sealed tube for 30 minutes. Palladium (II) acetate (467 mg) was then added and the reaction mixture was heated up to 100° C. for 18 hours. After addition of water and 1M HCl, the solution was extracted twice with ethyl acetate. Organic layers were washed twice with brine and dried over sodium sulfate. Solvents were removed in vacuo and the residue was purified by automatic flash chromatography on silica gel (cyclohexane/ethyl acetate+0.1% Acetic acid 1/0 to 100/0). Final compound 4-{(E)-2-[2,2,2-Trifluoro-1-(3-trifluoromethyl-phenyl)-ethylcarbamoyl]-vinyl}-naphtalene-1-carboxylic acid was washed with a 75/25 $CH_2Cl_2$/MeOH mixture to afford a white solid (1.2 g). MS (HPLC/MS): 468 ($MH^+$). Retention time: 1.76 min Method B.

Step D:

N-(Cyclopropylmethyl)amine (18 μl), PyBOP (98 mg) and Hüning's Base (119 μl) is added to a solution of 4-{2-[2,2,-Trifluoromethyl-phenyl)-ethylcarbamoyl]-ethyl}-naphtalene-1-carboxylic acid (80 mg). After 2 hours at room temperature, the reaction is quenched with water. The reaction mixture is extracted three times with dichloromethane. The combined organic phases are extracted with a saturated solution of $NaHCO_3$ and with a saturated aqueous solution of NaCl, dried over $Na_2SO_4$ and concentrated in vacuo. The crude product is purified on a semi-preparative HPLC to yield N-(cyclopropylmethyl)-4-[(1E)-2-({2,2,2-trifluoro-1-[3-(trifluoromethyl)phenyl]ethyl}carbamoyl)eth-1-en-1-yl]naphthalene-1-carboxamide (55 mg) as a white foam. MS (HPLC/MS): 521 ($MH^+$). Retention time: 1.83 min Method B.

EXAMPLE 2

This example illustrates the preparation of N-((1S,2S)-2-fluorocyclopropyl)-2-methyl-4-((E)-3-oxo-3-((2,2,2-trifluoro-1-(3-(trifluoromethyl)phenyl)ethyl)amino)prop-1-en-1-yl)benzofuran-7-carboxamide (Compound 3.8 in Table 3)

Step A

To a solution of methyl 4-bromo-2-hydroxybenzoate (1 g, 4.3 mmol) in DMF (20 mL) was added potassium carbonate (1.782 g, 12.9 mmol). After 15 min, 3-bromoprop-1-yne (80% in toluene) (856 mg, 6 mmol) was added and the whole was stirred at room temperature overnight. The reaction mixture was concentrated in vacuum, dissolved in water and then extracted with EtOAc. The combined organic phases were washed with a saturated solution of NaCl, dried over $MgSO_4$ and concentrated in vacuo to give 1.19 g of methyl 4-bromo-2-(prop-2-yn-1-yloxy)benzoate quantitatively.

Step B:

To the mixture of methyl 4-bromo-2-(prop-2-yn-1-yloxy) benzoate (1.160 g, 4.31 mmol) and cesium fluoride (654 mg, 4.31 mmol) placed in a flask flushed with $N_2$ was added N,N'-dimethylaniline (10 mL) and the mixture was heated at 190° C. for 4 h in the microwave. The reaction mixture was concentrated in vacuo, dissolved in water and extracted with EtOAc. The combined organic phases were acidified with 1N HCl, washed with brine, dried over MgSO4 and concentrated in vacuo. The crude material was purified by preparative HPLC to give 510 mg of methyl 4-bromo-2-methylbenzofuran-7-carboxylate in 44%.

Step C:

A solution of methyl4-bromo-2-methylbenzofuran-7-carboxylate (540 mg, 2 mmol), N-[2,2,2-trifluoro-1-(3-trifluoromethyl-phenyl)-ethyl]acrylamide (595 mg, 2 mmol) and triethylamine (2.45 mL, 17.6 mmol) in DMF (5 mL) was degassed with $N_2$ before palladium acetate (135 mg, 0.6 mmol) and triphenylphosphine (105 mg, 0.4 mmol) were added. The reaction mixture was heated at 100° C. for 2 h, then dissolved in water. The aqueous phase was extracted with DCM. The combined organic phases were washed with brine, dried over $MgSO_4$ and concentrated in vacuo. The crude material was purified by preparative HPLC to give 219 mg of (E)-methyl 2-methyl-4-(3-oxo-3-((2,2,2-trifluoro-1-(3-(trifluoromethyl)phenyl)-ethyl)amino)prop-1-en-1-yl)benzofuran-7-carboxylate in 22% yield.

Step D:

To a solution of (E)-methyl 2-methyl-4-(3-oxo-3-((2,2,2-trifluoro-1-(3-(trifluoromethyl)phenyl)-ethyl)amino)prop-1-en-1-yl)benzofuran-7-carboxylate (219 mg, 0.45 mmol) in THF (8 mL) was added 1N NaOH (6.75 mL, 6.75 mmol) and the reaction mixture was stirred at room temperature overnight. Then 2N HCl was added until pH1-2 and the aqueous phase was extracted with EtOAc. The combined orgaic phases were washed brine, dried over $MgSO_4$ and concentrated in vacuo to give 185 mg of (E)-2-methyl-4-(3-oxo-3-((2,2,2-trifluoro-1-(3-(trifluoromethyl)phenyl)ethyl)amino)prop-1-en-1-yl)benzofuran-7-carboxylic acid in 87% yield.

Step E:

A solution of (E)-2-methyl-4-(3-oxo-3-((2,2,2-trifluoro-1-(3-(trifluoromethyl)phenyl)ethyl)-amino)prop-1-en-1-yl) benzofuran-7-carboxylic acid (80 mg, 0.17 mmol), (1R,2S)-2-fluorocyclopropan-1-amine toluene sulphonate (49 mg, 0.2 mmol), HATU (71 mg, 0.19 mmol) and N,N-diisiopropylethylamine (DIPEA, 0.12 mL, 0.68 mmol) in DMF (3 mL) was stirred at room temperature overnight. The reaction mixture was dissolved in water and extracted with DCM. The combined organic phases were washed with a saturated solution of $NaHCO_3$, brine, dried over $MgSO_4$ and concentrated in vacuo. The crude material was purified by preparative HPLC to give 38 mg of (E)-N-(2-fluorocyclopropyl)-2-methyl-4-(3-oxo-3-((2,2,2-trifluoro-1-(3-(trifluoromethyl)-phenyl)ethyl)amino)prop-1-en-1-yl) benzofuran-7-carboxamide in 42% yield as a white solid. MS (HPLC/MS): 529 ($MH^+$). Retention time: 1.81 min Method B.

EXAMPLE 3

This example illustrates the preparation of (E)-N,N-diethyl-3-(3-oxo-3-((2,2,2-trifluoro-1-(3-(trifluoromethyl) phenyl)ethyl)amino)prop-1-en-1-yl)benzo[c]thiophene-1-carboxamide (Compound 3.10 in Table 3)

Step A:

To a solution of 1,3-dichlorobenzo[c]thiophene (280 mg, 1.38 mmol) in THF (5 mL) under $N_2$ at −78° C. was added n-BuLi (0.61 mL, 1.38 mmol). After 30 min, initiate —$CO_2$ was added by bubbling and the mixture was stirred at room temperature for 1 h. The solution was acidified with 2M HCl. The aqueous phase was extracted with ethyl acetate. The combined organic phases were washed with brine, dried over MgSO$_4$ and concentrated in vacuo to give 147 mg of 3-chlorobenzo[c]thiophene-1-carboxylic acid in 50% yield.

Step B:

A solution of 3-chlorobenzo[c]thiophene-1-carboxylic acid (147 mg, 0.69 mmol), diethylamine hydrochloride (0.13 mL, 0.83 mmol), 1-[Bis(dimethylamino)methylene]-1H-1,2,3-triazolo[4,5-b]pyridinium 3-oxid hexafluorophosphate (HATU, 288 mg, 0.76 mmol) and DIPEA (0.47 mL, 2.76 mmol) in DMF (3 mL) was stirred at room temperature overnight. The reaction mixture was dissolved in water. The aqueous phase was extracted with DCM and the combined organic phases were washed with a saturated solution of NaHCO$_3$, brine, dried over MgSO$_4$ and concentrated in vacuo. The crude material was purified by preparative LCMS to give 81 mg of 3-chloro-N,N-diethylbenzo[c]thiophene-1-carboxamide in 44% yield.

Step C:

A solution of 3-chloro-N,N-diethylbenzo[c]thiophene-1-carboxamide (43 mg, 0.16 mmol), N-[2,2,2-trifluoro-1-(3-trifluoromethyl-phenyl)-ethyl]acrylamide (71 mg, 0.24 mmol) and tetra-butyl ammonium chloride (89 mg, 0.32 mmol) in dioxane (1 mL) was degassed with N$_2$ before palladium acetate (7 mg, 0.032 mmol) and Dave-Phos (37 mg, 0.096 mmol) were added. The reaction mixture was heated at 80° C. overnight, and then dissolved in water. The aqueous phase was extracted with DCM. The combined organic phases were washed with brinel, dried over MgSO$_4$ and concentrated in vacuo. The crude material was purified by preparative Liquid chromatography-mass spectrometry (LCMS) and then preparative HPLC to give 18 mg of (E)-N,N-diethyl-3-(3-oxo-3-((2,2,2-trifluoro-1-(3-(trifluoromethyl)phenyl)ethyl)amino)prop-1-en-1-yl)benzo[c]thiophene-1-carboxamide in 21% yield as a white solid. MS (HPLC/MS): 529 (MH$^+$). Retention time: 1.96 min Method B.

The substances named in the following Table 1 are prepared analogously to the above-described methods. The compounds are of formula

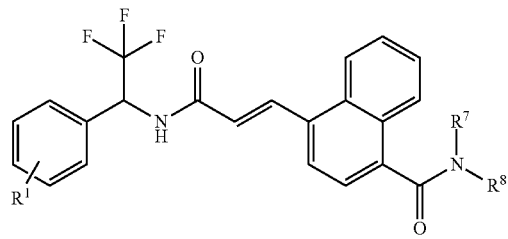

wherein the meaning of R$_1$, R$_5$ and R$_6$ are given in Table 1.1

The following physical data are obtained according to the above-described HPLC/MS characterization process.

TABLE 1.1

| Ex. No. | R$^1$ | R$^7$ | R$^8$ | m/z: [M + H$^+$] | R$_t$ [min] (Method) | Physical state |
|---|---|---|---|---|---|---|
| 1.1 | 3-CF$_3$ | H | cyclopropylmethyl | 521 | 1.83 (B) | foam |
| 1.2 | 3-CF$_3$ | H | (pyridin-2-yl)methyl | 558 | 1.53 (B) | solid |
| 1.3 | 3-CF$_3$ | H | (furan-2-yl)methyl | 547 | 1.82 (B) | foam |
| 1.4 | 3-CF$_3$ | H | benzyl | 557 | 1.91 (B) | foam |
| 1.5 | 3-CF$_3$ | H | cyclopropyl | 507 | 1.74 (B) | solid |
| 1.6 | 3-CF$_3$ | H | propargyl | 505 | 1.75 (B) | foam |
| 1.7 | 3-CF$_3$ | H | 2,2,2-trifluoroethyl | 549 | 1.85 (B) | foam |
| 1.8 | 3-CF$_3$ | H | 4-fluorobenzyl | 561 | 1.97 (B) | foam |
| 1.9 | 3-CF$_3$ | H | oxetan-3-yl | 523 | 1.63 (B) | solid |

TABLE 1.1-continued

| Ex. No. | R¹ | R⁷ | R⁸ | m/z: [M + H⁺] | $R_t$ [min] (Method) | Physical state |
|---|---|---|---|---|---|---|
| 1.10 | 3-CF$_3$ | H | thietanyl | 539 | 1.82 (B) | solid |
| 1.11 | 3-CF3 | H | —CH$_2$CN | 506 | 1.71 (B) | solid |
| 1.12 | 3-CF3 | H | —CH$_2$CHF$_2$ | 531 | 1.79 (B) | Resin |
| 1.13 | 3-CF3 | H | —CH$_2$CH=CH$_2$ (propyl) | 495 | 1.75 (B) | Solid |
| 1.14 | 3-CF3 | H | tetrahydropyran-4-yl | 551 | 1.71 (B) | Solid |
| 1.15 | 3-CF3 | H | isobutyl | 523 | 1.90 (B) | Foam |
| 1.16 | 3-CF3 | —(CH$_2$)$_5$— | | 535 | 1.96 (B) | Foam |
| 1.17 | 3-CF$_3$ | —(CH$_2$)$_2$—O—(CH$_2$)$_2$— | | 537 | 1.74 (B) | Foam |
| 1.18 | 3-CF$_3$ | —(CH$_2$)$_4$— | | 521 | 1.83 (B) | Foam |
| 1.19 | 3-CF$_3$ | H | pyridin-2-yl | 544 | 1.86 (B) | Solid |
| 1.20 | 3-CF$_3$ | —(CH$_2$)$_2$—N(CH$_3$)—(CH$_2$)$_2$— | | 550 | 1.27 (B) | Foam |
| 1.21 | 3-CF$_3$ | H | (3S)-2-oxopyrrolidin-3-yl | 550 | 1.55 (B) | Solid |
| 1.22 | 3-CF$_3$ | H | —CH$_2$C(O)NHCH$_2$CF$_3$ | 606 | 1.74 (B) | Foam |
| 1.23 | 3-CF$_3$ | H | 1-Boc-azetidin-3-yl | 622 | 1.91 (B) | Foam |
| 1.24 | 3-CF$_3$ | —(CH$_2$)$_2$—NH—(CH$_2$)$_2$— | | 536 | 1.30 (B) | Foam |
| 1.25 | 3-CF$_3$ | —(CH$_2$)$_3$— | | 507 | 1.75 (B) | Solid |
| 1.26 | 3-CF$_3$ | H | 1-cyanocyclopropyl | 532 | 1.78 (B) | Solid |
| 1.27 | 3-CF$_3$ | H | isopropyl | 509 | 1.82 (B) | Solid |

TABLE 1.1-continued
| Ex. No. | R¹ | R⁷ | R⁸ | m/z: [M + H⁺] | R_t [min] (Method) | Physical state |
|---|---|---|---|---|---|---|
| 1.28 | 3-CF₃ | H |  | 523 | 1.95 (B) | Solid |
| 1.29 | 3-CF₃ | H |  | 521 | 1.87 (B) | Solid |
| 1.30 | 3-CF3 | H |  | 511 | 1.57 (B) | Solid |
| 1.32 | 3-CF3 | H |  | 536 | 1.28 (B) | Foam |
| 1.34 | 3-CF3 | H | 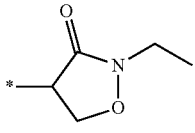 [SMILES: *C1CON(CC)C1=O] | 580 | 1.71 (B) | Solid |
| 1.35 | 3-CF3 | H |  | 557 | 1.86 (B) | Solid |
| 1.36 | 3-CF3 | H |  | 539 | 1.80 (B) | Solid |
| 1.37 | 3-CF3 | H |  | 561 | 2.06 (B) | Solid |
| 1.38 | 3-CF3 | H | H | 467 | 1.62 (B) | Solid |
| 1.39 | 3-CF3 |  |  | 523 | 1.88 (B) | Foam |
| 1.40 | 3-CF3 | H |  | 525 | 1.71 (B) | Solid |
| 1.41 | 3-CF3 | H |  | 535 | 2.16 (B) | Solid |
| 1.42 | 3-CF3 | H |  | 589 | 1.97 (B) | Solid |
| 1.43 | 3-CF3 | H |  | 554 | 1.86 (B) | Solid |
| 1.44 | 3-CF3 | H |  | 546 | 1.83 (B) | Foam |
| 1.45 | 3-CF3 | H |  | 567 | 1.87 (B) | Foam |

TABLE 1.1-continued
| Ex. No. | R¹ | R⁷ | R⁸ | m/z: [M + H⁺] | R_t [min] (Method) | Physical state |
|---|---|---|---|---|---|---|
| 1.46 | 3-CF3 | H | 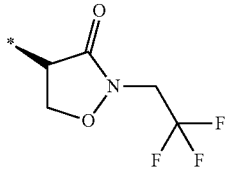 | 634 | 1.84 (B) | Foam |
| 1.47 | 3-CF₃ | | —CH₂—(C(CF₂))₂—CH₂— | 593 | 1.98 (B) | Foam |
| 1.48 | 3-CF₃ | H | 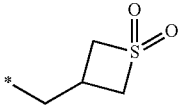 | 585 | 1.67 (B) | Foam |
| 1.49 | 3-CF₃ | CH₃ | CH₃ | 495 | 1.75 (B) | Foam |
| 1.50 | 3-CF₃ | H | 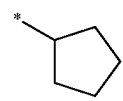 | 535 | 1.92 (B) | Solid |
| 1.51 | 3-CF₃ | H | 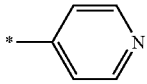 | 544 | 1.39 (B) | Solid |
| 1.52 | 3-CF₃ | H | 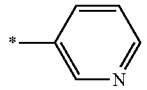 | 544 | 2.09 (B) | Solid |
| 1.53 | 3-CF₃ | | —CH(CF₃)—(CH₂)₃— | 589 | 2.02 (B) | Foam |
| 1.54 | 4-CF₃ | H |  | 507 | 1.73 (B) | Solid |
| 1.55 | 3-CF₃ | H |  | 453 | 1.59 (B) | Solid |
| 1.56 | 3-Br | H |  | 517 | 1.71 (B) | Solif |
| 1.57 | 4-OCH₃ | H |  | 470 | 1.57 (B) | Solid |
| 1.58 | 3-CH₃ | H |  | 453 | 1.64 (B) | Powder |
| 1.59 | 3-Cl | H |  | 473 | 1.67 (B) | Powder |
| 1.60 | 3-tert.-butyl | H |  | 495 | 1.86 (B) | Powder |
| 1.61 | 3-OCF₃ | H |  | 523 | 1.74 (B) | Solid |
| 1.62 | 3,5-di-Cl | H |  | 507 | 1.85 (B) | Powder |

TABLE 1.1-continued
| Ex. No. | R¹ | R⁷ | R⁸ | m/z: [M + H⁺] | $R_t$ [min] (Method) | Physical state |
|---|---|---|---|---|---|---|
| 1.63 | 3,4-di-Cl | H |  | 507 | 1.82 (B) | Powder |
| 1.64 | 3,4,5-tri-Cl | H |  | 541 | 1.96 (B) | Powder |
| 1.65 | 3-F | H |  | 457 | 1.64 (B) | Solid |
| 1.66 | 3-CF₃-4-Cl | H |  | 541 | 1.86 (B) | Solid |
| 1.67 | 3-OCH₃ | H |  | 469 | 1.59 (B) | Solid |
| 1.68 | 3-(4'-CF₃-phenyl) | H |  | 583 | 1.98 (B) | Solid |
| 1.69 | 3-(3',5'-di-Cl-phenyl) | H |  | 583 | 2.13 (B) | Solid |
| 1.70 | 3,5-di-Cl-4-F— | H |  | 525 | 1.85 (B) | Powder |
| 1.71 | 3-CF₃ | H | 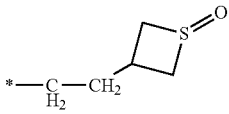 [SMILES: *CCC1CS(=O)C1] | 583 | 1.56 (B) | Solid |
| 1.72 | 3-CF₃ | H | 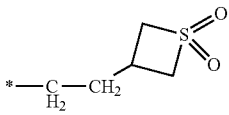 [SMILES: *CCC1CS(=O)(=O)C1] | 599 | 1.67 (B) | Solid |
| 1.73 | 3-CF₃ | H | 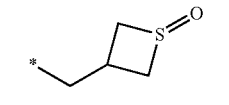 | 569 | 1.67 (B) | Foam |
| 1.74 | 3-CF₃ | H | 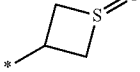 | 555 | 1.56 (B) | Foam |
| 1.75 | 3-CF₃ | H |  | 571 | 1.69 (B) | Solid |
| 1.76 | 3-CF₃ | H | —CH₂—CF₂—CH₂— | 543 | 1.85 (B) | Foam |

The substances named in the following Table 1.2 are prepared analogously to the above-described methods. The compounds are of formula

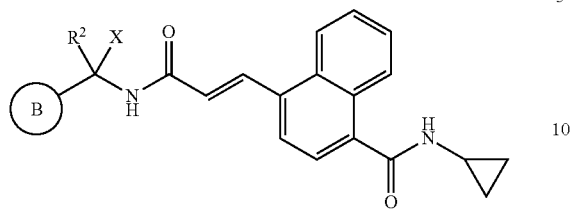

wherein the meaning of ring B, $R^2$, X and W are given in Table 1.2.

The following physical data are obtained according to the above-described HPLC/MS characterization process.

| Ex. No. | Ring B | $R^2$ | X | m/z: [M + H⁺] | $R_t$ [min] (Method) | Physical state |
|---|---|---|---|---|---|---|
| 1.77 | F₃C—⌬—* | CH₃ | CH₃ | 467 | 1.66 (B) | Solid |
| 1.78 | 2-pyridyl-* | H | CF₃ | 440 | 1.20 (B) | Solid |
| 1.79 | 3-pyridyl-* | H | CF₃ | 440 | 1.42 (B) | Solid |
| 1.80 | F₃C—⌬—* | H | CH₂OCH₃ | 483 | 1.56 (B) | Solid |
| 1.81 | F₃C—⌬—* | H | H | 439 | 1.54 (B) | Solid |
| 1.82 | 1-naphthyl-* | H | CF₃ | 489 | 1.73 (B) | Solid |
| 1.83 | 2-naphthyl-* | H | CF₃ | 489 | 1.71 (B) | Solid |
| 1.84 | F₃C—⌬—* | H | C(O)OCH₃ | 447 | 1.52 (B) | Solid |
| 1.85 | 3-Cl-5-Br-phenyl-* | H | CF₃ | 553 | 1.87 (B) | Powder |

-continued

| Ex. No. | Ring B | R² | X | m/z: [M + H⁺] | R_t [min] (Method) | Physical state |
|---|---|---|---|---|---|---|
| 1.86 | 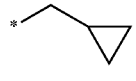 | H | CF₃ | 597 | 1.90 (B) | Powder |

The substances named in the following Table 2 are prepared analogously to the above-described methods. The compounds are of formula

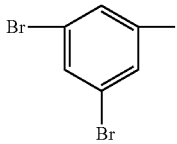

wherein the meaning of R₇ and R₈ are given in Table 2.

The following physical data are obtained according to the above-described HPLC/MS characterization process.

TABLE 2

| Example No. | R⁷ | R⁸ | m/z: [M + H⁺] | R_t [min] (Method) | Physical state |
|---|---|---|---|---|---|
| 2.1 | H | 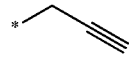 [SMILES: *CC#C] | 491 | 1.82 (B) | foam |
| 2.2 | H | 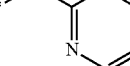 | 475 | 1.73 (B) | foam |
| 2.3 | H |  | 528 | 1.45 (B) | foam |

TABLE 2-continued

| Example No. | R⁷ | R⁸ | m/z: [M + H⁺] | R_t [min] (Method) | Physical state |
|---|---|---|---|---|---|
| 2.4 | H | 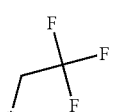 | 477 | 1.71 (B) | solid |
| 2.5 | H | 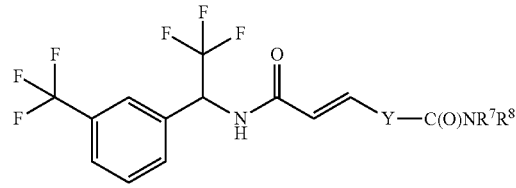 | 519 | 1.83 (B) | solid |

The substances named in the following Table 3 are prepared analogously to the above-described methods. The compounds are of formula

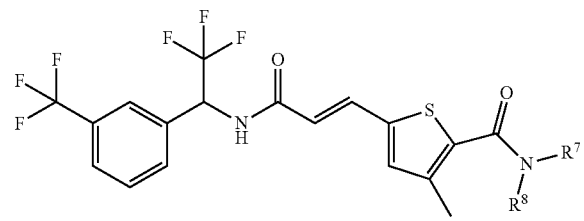

wherein the meaning of Y, R⁷ and R⁸ are given in Table 3.

The following physical data are obtained according to the above-described HPLC/MS characterization process.

| Ex. No. | Y—C(O)— | R⁷ | R⁸ | m/z: [M + H⁺] | R_t [min] (Method) | Physical state |
|---|---|---|---|---|---|---|
| 3.1 | 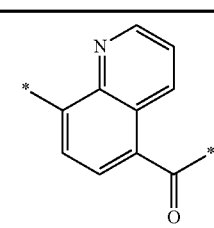 |  | H | 496 | 1.65 (B) | Solid |
| 3.2 | 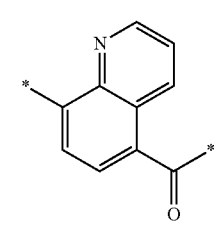 [SMILES: *C(=O)c1ccc(*)c2ncccc12] |  | H | 508 | 1.66 (B) | Solid |

-continued

| Ex. No. | Y—C(O)— | R⁷ | R⁸ | m/z: [M + H⁺] | R_t [min] (Method) | Physical state |
|---|---|---|---|---|---|---|
| 3.3 | quinoline-5-yl carbonyl (8-position attachment) | cyclopropylmethyl | H | 522 | 1.75 (B) | Solid |
| 3.4 | quinoline-5-yl carbonyl (8-position attachment) | 2,2,2-trifluoroethyl | H | 550 | 1.79 (B) | Foam |
| 3.5 | quinoline-8-yl carbonyl (5-position attachment) | 2,2,2-trifluoroethyl | H | 550 | 1.92 (B) | Solid |
| 3.6 | quinoline-8-yl carbonyl (5-position attachment) | cyclopropylmethyl | H | 522 | 1.91 (B) | Foam |
| 3.7 | quinoline-8-yl carbonyl (5-position attachment) | ethyl | H | 496 | 1.80 (B) | Foam |
| 3.8 | 2-methylbenzofuran-7-yl carbonyl | 2-fluorocyclopropyl | H | 529 | 1.81 (B) | Solid |
| 3.9 | 2-methylbenzofuran-7-yl carbonyl | 3,3-difluorocyclobutyl | H | 561 | 1.72 (B) | Solid |

-continued

| Ex. No. | Y—C(O)— | R⁷ | R⁸ | m/z: [M + H⁺] | R_t [min] (Method) | Physical state |
|---|---|---|---|---|---|---|
| 3.10 | (1-substituted benzo[b]thiophene-2-carbonyl) | ethyl | ethyl | 529 | 1.96 (B) | Solid |

The substances named in the following Table 4 are prepared analogously to the above-described methods. The following physical data are obtained according to the above-described HPLC/MS characterization process.

TABLE 4

| Ex. No. | Compound of formula | m/z: [M + H⁺] | R_t [min] (Method) | Physical state |
|---|---|---|---|---|
| 4.1 | R-enantiomer[1] | 507 | 1.76 (B) | Foam |
| 4.2 | S-enantiomer[1] | 507 | 1.75 (B) | Foam |
| 4.3 | | 539 | 2.84 (B) | Solid |
| 4.4 | | 507 | 1.73 (B) | Solid |

[1] Prepared by performing the synthesis with a chiral amine of formula (II).

BIOLOGICAL EXAMPLES

1. Activity In Vitro Against *Ctenocephalides felis* (Cat Flea)

A mixed adult population of fleas is placed in a suitably formatted 96-well plate allowing fleas to access and feed on treated blood via an artificial feeding system. Fleas are fed on treated blood for 24 hours, after which the compound effect is recorded. Insecticidal activity is determined on the basis of the number of dead fleas recovered from the feeding system. In this test the example compounds showed more than 80% ($EC_{80}$) efficacy at 100 ppm.

2. Activity In Vitro Against *Rhipicephalus sanguineus* (Dog Tick)

A clean adult tick population is used to seed a suitably formatted 96-well plate containing the test substances to be evaluated for antiparasitic activity. Each compound is tested by serial dilution in order to determine its minimal effective dose (MED). Ticks are left in contact with the test compound for 10 minutes and are then incubated at 28° C. and 80% relative humidity for 7 days, during which the test compound effect is monitored. Acaricidal activity is confirmed if adult ticks are dead.

In this test the example compounds showed more than 80% ($EC_{80}$) efficacy at 640 ppm.

3—Activity In Vitro Against *Lepeophtheirus Salmonis* at Copeodid Stage

Sea lice copepodids were used to seed a 96-well plate containing the test substances to be evaluated for antiparasitic activity. Each compound was tested by serial dilution in order to determine its minimal effective dose (MED). Copepodids were left in contact with the test compound diluted in sea water for 1 hour. They were then incubated in untreated sea water for 48 h. Efficacy against sea lice was then confirmed if no copepodid moved over a period of 80 seconds.

In this test the following examples showed efficacy (EC80) at 50 ppb: 1.1, 1.3, 1.7, 1.10, 1.13, 1.27, 1.34, 1.35, 1.36, 1.40, 1.44, 1.46, 1.56, 1.58, 1.62, 1.63, 1.66, 1.82, 2.4, 3.2, 4.1; at 5 ppb: 1.5, 1.7, 1.41, 1.43, 1.64, 1.65; at 0.5 ppb: 1.26, 1.61.

4—Activity In Vivo Against *Ctenocephalides felis* (Cat Flea) on Mongolian Gerbils (*Meriones unguiculatus*) (Per Oral Application)

On day 0, gerbils are treated orally by gavage with the test compound formulated at a given dose. Immediately after treatment, they are infested with a mixed adult population of cat fleas. Evaluation of efficacy is performed after 48 h infestation by counting the numbers of live fleas recovered from the gerbils. Efficacy is expressed as comparison with a placebo treated group using the Abbot's formula.

In this test the example compounds showed more than 80% ($EC_{80}$) efficacy at 32 mg/kg: 1.1, 1.5, 1.6, 1.7, at 10 mg/kg: 1.12, 1.35, 1.36, 1.40.

5—Activity In Vivo Against *Rhipicephalus sanguineus* Nymphs on Mongolian Gerbils (*Meriones unguiculatus*) (Per Oral Application)

One day before treatment, gerbils are infested with nymphs of *R. sanguineus*. On day 0, the animals are treated orally by gavage with the test compound formulated at a given dose. Ticks are left on the animals until full repletion. Seven days after infestation nymphs dropped off fully engorged are collected and counted. They are kept until molting to also evaluate growth regulating activity of the test compound. Efficacy in killing (and growth regulating) is expressed as a tick number (and molted tick number) reduction in comparison with a placebo treated group, using the Abbot's formula. In this test the following examples showed more than 90% ($EC_{90}$) g at 32 mg/kg: 1.34, 1.35, 1.36; at 10 mg/kg: 1.1, 1.39, 1.40.

6—Activity In Vivo Against Lice (*Polyplax serrata*) in Mice (Topical)

Mice naturally infected with *P. serrata* are treated with the formulated test compound on day 0 by spray or pour-on application. On day+4 and +14, efficacy is evaluated by counting the number of live lice under a binocular. Efficacy at the two time points is expressed as a comparison of lice numbers counted on the same mouse before treatment, using the Henderson & Tilton formula, taking also into account lice numbers found on mice treated with the empty formulation (placebo group). In this test the following examples showed more than 80% ($EC_{90}$) efficacy at 10 mg/kg: 1.1, 1.5, 1.7, 1.8, 1.14, 1.18, 1.25, 1.26, at 3.2 mg/kg: 1.12, 1.13, 1.15, 1.27, 1.29, 1.35, 1.36, 1.39, 1.40.

The invention claimed is:

1. A compound of formula

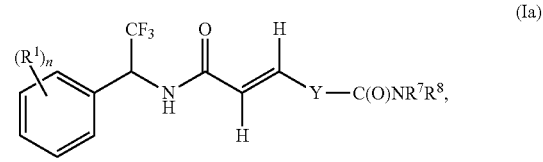

(Ia)

including all geometric and stereoisomers, N-oxides, S-oxides, salts and prodrugs thereof, $R^1$ is independently halogen, cyano (—CN), nitro (—$NO_2$), $C_1$-$C_6$-alkyl, $C_3$-$C_6$-cycloalkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, N-mono- or N,N-di-$C_1$-$C_6$-alkylamino, $C_1$-$C_6$ alkoxycarbonyl, $C_1$-$C_6$-alkylcarbonyl, aminosulfonyl, $C_1$-$C_6$-alkylaminosulfonyl, $C_1$-$C_6$-alkylsulfonylamino or phenyl which is unsubstituted or substituted by halogen, cyano, nitro, $C_1$-$C_4$-haloalkyl, $C_1$-$C_4$-haloalkoxy or $C_1$-$C_4$-haloalkylthio; or $R^1$ is a $C_1$-$C_4$ carbon chain which optionally contains 1-2 heteroatoms from the group of N, S, and O, which is bonded to two adjacent ring positions and which forms an aliphatic, aromatic, heteroaromatic or heterocyclic ring which is optionally mono- or polysubstituted by $C_1$-$C_6$-alkyl or halogen, in which case n is 2;

Y is a radical of formula

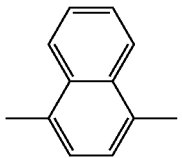
(IIa')

where the second (right-hand) connection site in each case is connected to the C(O)NR$^7$R$^8$ moiety;

R$^7$ is H, C$_1$-C$_6$-alkyl which is unsubstituted or substituted by halogen, C$_1$-C$_4$-alkoxy, C$_1$-C$_2$-alkylthio, cyano, nitro, amino or N-mono- or N,N-di-C$_1$-C$_4$alkylamino, or is C$_2$-C$_4$-alkenyl, C$_2$-C$_4$-alkynyl or C$_3$-C$_6$-cycloalkyl;

R$^8$ is H; a group —CH═N—OR$^9$; a radical Q; a radical Q$^1$; or is C$_1$-C$_6$-alkyl, C$_2$-C$_6$-alkenyl, C$_2$-C$_6$-alkynyl, C$_3$-C$_6$-cycloalkyl, C$_4$-C$_7$-alkylcycloalkyl, C$_4$-C$_7$-cycloalkylalkyl, C$_5$-C$_{10}$-bicyclo-alkylene or C$_3$-C$_6$-cycloalkanone which is each unsubstituted or substituted in the alkyl, cycloalkyl, alkenyl or alkynyl moiety by halogen, hydroxy, carboxy (COOH), C$_1$-C$_4$-alkyl, C$_1$-C$_6$-alkoxy, C$_1$-C$_6$-haloalkoxy, C$_1$-C$_6$-alkylthio, C$_1$-C$_6$-haloalkylthio, C$_1$-C$_6$-alkylsulfinyl, C$_1$-C$_6$-alkylsulfonyl, cyano, nitro, amino, N-mono- or N,N-di-C$_1$-C$_6$-alkylamino, C$_3$-C$_6$-cycloalkylamino, C$_1$-C$_6$-alkoxycarbonyl, C$_2$-C$_6$-alkylcarbonyl, C$_1$-C$_6$-alkylcarbonylamino, aminosulfonyl, N-mono- or N,N, di-C$_1$-C$_4$-alkylaminosulfonyl, a group —C(W')NR$^9$R$^{10}$ or a radical Q';

or R$^7$ and R$^8$ together are a group ═C(R$^{11}$)—NR$^{12}$R$^{13}$ or ═C(R$^{11}$)—C(NH$_2$)—OR$^{12}$); or R$^7$ and R$^8$ together with the N-atom to which they are attached, form a 3- to 7-membered ring which optionally contains a further heteroatom selected from the group consisting of N, S and O, and which ring is further unsubstituted or mono- or polysubstituted by C$_1$-C$_2$-alkyl, C$_1$-C$_2$-haloalkyl, C$_1$-C$_2$-alkoxy, hydroxy, halogen, cyano, nitro, N,N-di-C$_1$-C$_2$-alkylaminomethyl or N,N-di-C$_1$-C$_2$-alkylaminocarbonylmethyl;

Q and Q' are each independently a C$_6$-C$_{10}$-aryl, an aliphatic or aromatic 4-, 5- or 6-membered heterocyclic ring, or an aliphatic or aromatic 8-, 9- or 10-membered fused hetero-bicyclic ring, each of them being unsubstituted or mono- or polysubstituted by halogen, hydroxy, C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_2$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, cyano, nitro, amino, N-mono- or N,N-di-C$_1$-C$_6$-alkylamino, C$_3$-C$_6$-cycloalkylamino, COOH, C$_1$-C$_6$-alkoxycarbonyl, C$_2$-C$_6$-alkylcarbonyl, C$_1$-C$_6$-alkylcarbonyl-amino, aminocarbonyl, N-mono- or N,N-di-C$_1$C$_6$-alkylaminocarbonyl, aminosulfonyl, N-mono- or N,N, di-C$_1$-C$_4$-alkylaminosulfonyl, unsubstituted or halogen- or nitro-substituted phenyl-C$_1$-C$_4$-alkyl, 5- or 6-membered heterocyclyl-C$_1$-C$_4$-alkyl or a radical Q'';

Q'' is a C$_6$-C$_{10}$-carbocyclic ring or a 4-, 5- or 6-membered heterocyclic ring, each of them being aromatic or not, each of them being unsubstituted or mono- or polysubstituted by halogen, hydroxy, C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, cyano, nitro, amino, N-mono- or N,N-di-C$_1$-C$_6$-alkylamino, C$_3$-C$_6$-cycloalkylamino, COOH, C$_1$-C$_6$-alkoxycarbonyl, C$_2$-C$_6$-alkylcarbonyl, C$_1$-C$_6$-alkylcarbonyl-amino, aminocarbonyl, N-mono- or N,N-di-C$_1$C$_6$-alkylaminocarbonyl, aminosulfonyl, or N-mono- or N,N, di-C$_1$-C$_4$-alkylaminosulfonyl;

Q$^1$ is a radical

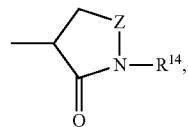

wherein Z is O or CH$_2$ and R$^{14}$ is H, C$_1$-C$_4$-alkyl, or C$_1$-C$_1$-haloalkyl, R$^9$ is H or C$_1$-C$_6$-alkyl;

R$^{10}$ is H, C$_1$-C$_6$-alkyl, C$_2$-C$_6$-alkenyl, C$_2$-C$_6$-alkynyl, C$_3$-C$_6$-cycloalkyl, C$_4$-C$_7$-alkylcycloalkyl or C$_4$-C$_7$-cycloalkylalkyl, which is each unsubstituted or substituted in the alkyl, alkenyl, alkynyl or cycloalkyl moiety by halogen, cyano, nitro, hydroxy, carboxy (COOH), C$_1$-C$_6$-alkoxy, C$_1$-C$_6$-haloalkoxy, C$_1$-C$_6$-alkylthio, C$_1$-C$_6$-haloalkylthio, C$_1$-C$_6$-alkylsulfinyl, C$_1$-C$_6$-alkylsulfonyl, amino, N-mono- or N,N-di-C$_1$-C$_6$-alkylamino, C$_3$-C$_6$-cycloalkylamino, C$_1$-C$_6$-alkoxycarbonyl, C$_2$-C$_6$-alkylcarbonyl, C$_1$-C$_6$-alkylcarbonylamino, aminocarbonyl, N-mono- or N,N-di-C$_1$C$_6$-alkylaminocarbonyl, aminosulfonyl, N-mono- or N,N, di-C$_1$-C$_4$-alkylamino-sulfonyl or a radical Q'';

R$^{11}$ is H C$_1$-C$_6$-alkyl or C$_1$-C$_6$-alkoxy, and

R$^{12}$ and R$^{13}$ are each independently of the other C$_1$-C$_6$-alkyl

W' is O or S.

2. A compound according to claim 1, wherein R$^7$ is H or C$_1$-C$_2$-alkyl.

3. A compound according to claim 2, wherein R$^8$ is (i) phenyl, which is unsubstituted or substituted by 1 or 2, same or different substituents selected from the group consisting of halogen, C$_1$-C$_2$-alkyl, C$_1$-C$_2$-haloalkyl, C$_1$-C$_2$-alkoxy, C$_1$-C$_2$-haloalkoxy, C$_1$-C$_2$-haloalkylthio, cyano, nitro, aminocarbonyl and unsubstituted or halogen-, C$_1$-C$_2$-alkyl-, C$_1$-C$_2$-haloalkyl-, C$_1$-C$_2$-alkoxy-, C$_1$-C$_2$-haloalkoxy-, cyano- or nitro-substituted phenyl and phenoxy; or is (ii) 2- or 3-furanyl, 2- or 3-thienyl, 1-, 2- or 3-pyrrolyl, 1-, 2-, 4- or 5-imidazolyl, 1- or 4-pyrazolyl, 2-, 4- or 5-thiazolyl, 1,2,4-triazol-3- or -4-yl, 1,2,3-triazin-1- or 2-yl, 2- 3- or 4-pyridyl or 4- or 5-pyrimidinyl, which is each unsubstituted or substituted by halogen, C$_1$-C$_2$-alkyl, C$_1$-C$_2$-haloalkyl, C$_1$-C$_2$-alkoxy, C$_1$-C$_2$-haloalkoxy, cyano, nitro, aminocarbonyl or C$_1$-C$_4$-alkoxycarbonyl; or is (iii) oxetanyl, thietanyl, thietanyl-1-oxide, thietanyl-1,1-dioxide, tetrahydrofuranyl, tetrahydro-thiophenyl, pyrrolidinyl, 2- or 3-pyrrolidonyl, 1,3-dioxolanyl, 1,2- or 1,3-oxazolidinyl, tetrahydropyranyl, piperidinyl, tetrahydrothiopyranyl, tetrahydrothiopyranyl-1,1-dioxide, morpholinyl, or 1,3- or 1,4-dioxanyl, which is each unsubstituted or substituted by halogen, C$_1$-C$_2$-alkyl, cyclopropyl, C$_1$-C$_2$-haloalkyl, C$_1$-C$_2$-alkoxy, C$_1$-C$_2$-haloalkoxy, cyano, nitro, or C$_1$-C$_4$-alkoxycarbonyl; or is (iv) $C_1$-$C_2$-alkyl which is unsubstituted or substituted by halogen; $C_1$-$C_2$-alkoxy; carboxy; $C_1$-$C_2$-alkoxycarbonyl; a radical —C(O)NHR$^{10}$ wherein R$^{10}$ is $C_1$-$C_4$-alkyl, halo-$C_1$-$C_2$-alkyl, cyano-$C_1$-$C_2$-alkyl, $C_2$-$C_3$-alkynyl or cyclopropylmethyl; phenyl which is unsubstituted or substituted by halogen, $C_1$-$C_2$-alkyl or $C_1$-$C_2$-alkoxy; or a heterocyclic ring selected from 2- or 3-furanyl, 2- or 3-thienyl, 1-, 2- or 3-pyrrolyl, 1-, 2-, 4- or 5-imidazolyl, 1- or 4-pyrazolyl, 2-, 4- or 5-thiazolyl, 1,2,4-triazol-3- or -4-yl, 1,2,3-triazin-1- or 2-yl, 2- 3- or 4-pyridyl, 4- or 5-pyrimidinyl, oxetanyl, thietanyl, thietanyl-1-oxide, thietanyl-1,1-dioxide and tetrahydrofuranyl, which is each unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano, nitro, aminocarbonyl or $C_1$-$C_4$-alkoxy-carbonyl; or is (v) $C_2$-$C_4$-alkenyl; (vi) $C_2$-$C_4$-alkynyl; (vii) $C_3$-$C_6$-cycloalkyl; or (viii) $C_3$-$C_6$-cycloalkyl-methyl.

4. A compound according to claim 3, wherein R$^8$ is (i) phenyl which is unsubstituted or substituted by halogen, $C_1$-$C_2$-alkyl or $C_1$-$C_2$-alkoxy;

(ii) 2-furanyl, 2-thiazoyl, 2- 3- or 4-pyridyl or 4- or 5-pyrimidinyl, each unsubstituted or substituted by $C_1$-$C_2$-alkyl, $C_1$-$C_2$-haloalkyl and $C_1$-$C_4$-alkoxycarbonyl;

(iii) oxetan-3-yl, thietan-3-yl, thietan-3-yl-1-oxide, thietan-3-yl-1,1-dioxide, or tetrahydrofuran-2- or -3-yl;

(iv) $C_1$-$C_2$-alkyl which is unsubstituted or substituted by chlorine; fluorine; $C_1$-$C_2$-alkoxy; —C(O)NHR$^{10}$ wherein R$^{10}$ is $C_1$-$C_4$-alkyl, 2,2,2-trifluoroethyl, cyanomethyl, propargyl or cyclopropylmethyl; 2-furanyl; 2-thiazoyl; 2- 3- or 4-pyridyl; 4- or 5-pyrimidinyl; oxetan-3-yl; thietan-3-yl; thietan-3-yl-1-oxide; thietan-3-yl-1,1-dioxide; tetrahydrofuran-2-yl; tetrahydrofuran-3-yl; or phenyl which is unsubstituted or substituted by halogen, $C_1$-$C_2$-alkyl or $C_1$-$C_2$-alkoxy;

(v) allyl; (vi) propargyl; (vii) $C_3$-$C_4$-cycloalkyl; or (viii) $C_3$-$C_4$-cycloalkylmethyl.

5. A compound according to claim 4, wherein R$^1$ is halogen, CH$_3$, CF$_3$, OCF$_3$, SCF$_3$ or SO$_2$CH$_3$, n is an integer 1 or 2, R$^7$ is H or $C_1$-$C_2$-alkyl, in particular H, and R$^8$ is (i) phenyl which is unsubstituted or substituted by halogen, $C_1$-$C_2$-alkyl or $C_1$-$C_2$-alkoxy;

(ii) 2-furanyl, 2-thiazoyl, 2- 3- or 4-pyridyl or 4- or 5-pyrimidinyl, each unsubstituted or substituted by $C_1$-$C_2$-alkyl, $C_1$-$C_2$-haloalkyl and $C_1$-$C_4$-alkoxycarbonyl;

(iii) oxetan-3-yl, thietan-3-yl, thietan-3-yl-1-oxide, thietan-3-yl-1,1-dioxide, or tetrahydrofuran-2- or -3-yl;

(iv) $C_1$-$C_2$-alkyl which is unsubstituted or substituted by chlorine; fluorine; $C_1$-$C_2$-alkoxy; —C(O)NHR$^{10}$ wherein R$^{10}$ is $C_1$-$C_4$-alkyl, 2,2,2-trifluoroethyl, cyanomethyl, propargyl or cyclopropylmethyl; 2-furanyl; 2-thiazoyl; 2- 3- or 4-pyridyl; 4- or 5-pyrimidinyl; oxetan-3-yl; thietan-3-yl; thietan-3-yl-1-oxide; thietan-3-yl-1,1-dioxide; tetrahydrofuran-2-yl; tetrahydrofuran-3-yl; or phenyl which is unsubstituted or substituted by halogen, $C_1$-$C_2$-alkyl or $C_1$-$C_2$-alkoxy;

(v) allyl; (vi) propargyl; (vii) $C_3$-$C_4$-cycloalkyl; or (viii) $C_3$-$C_4$-cycloalkylmethyl.

6. A compound according to claim 1 of formula

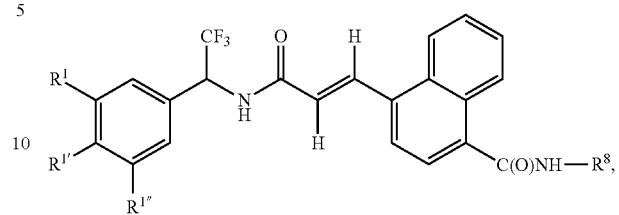

(Ib)

wherein R$^1$ is halogen, CF$_3$ or OCF$_3$;
R$^{1'}$ and R$^{1''}$ are each independently H or halogen; and
R$^8$ is as defined in claim 1.

7. A compound according to claim 6, wherein R$^8$ is
(i) $C_1$-$C_3$-alkyl which is unsubstituted or substituted by fluorine or cyano;
(ii) $C_3$-$C_4$-cycloalkyl, which is unsubstituted or substituted by methyl, halogen or cyano;
(iii) 2-furanyl;
(iv) thietan-4-yl or thietan-3-yl-methyl; or
(v) a radical

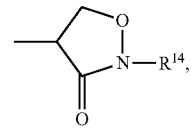

wherein R$^{14}$ is $C_1$-$C_2$-alkyl or halo-$C_1$-$C_2$-alkyl.

8. A compound according to claim 7, wherein R$^1$ is CF$_3$ and R$^{1'}$ and R$^{1''}$ are each H.

9. Method of controlling parasites in and on vertebrates, which comprises applying to the vertebrates a pharmaceutical effective amount of at least one compound of claim 1.

10. The method according to claim 9, wherein the parasites are sea lice on fish.

11. A compound according to claim 1 of formula

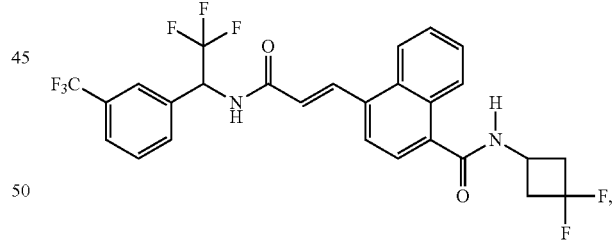

or a salt or an enantiomer thereof.

12. A compound according to claim 1

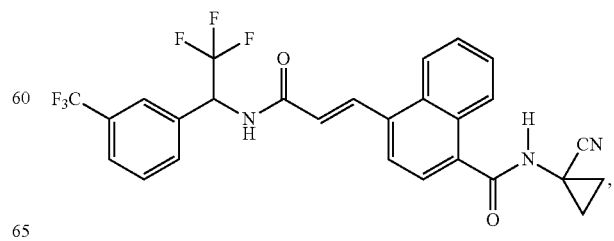

or a salt or an enantiomer thereof.

13. A compound according to claim 1
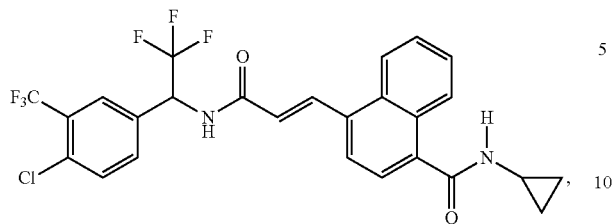
or a salt or an enantiomer thereof.
* * * * *

UNITED STATES PATENT AND TRADEMARK OFFICE
CERTIFICATE OF CORRECTION

PATENT NO. : 9,491,941 B2
APPLICATION NO. : 14/649268
DATED : November 15, 2016
INVENTOR(S) : Emilie Dupont et al.

It is certified that error appears in the above-identified patent and that said Letters Patent is hereby corrected as shown below:

In the Claims

In Claim 1, Column 50, Lines 55-56, delete "$C_1$-$C_6$ alkoxycarbonyl," and insert -- $C_1$-$C_6$-alkoxycarbonyl, --, therefor.

In Claim 1, Column 51, Line 17, delete "N,N-di-$C_1$-$C_4$alkylamino," and insert -- N,N-di-$C_1$-$C_4$-alkylamino, --, therefor.

In Claim 1, Column 51, Line 32, delete "N,N," and insert -- N,N- --, therefor.

In Claim 1, Column 51, Line 36, delete "=C($R^{11}$)–C($NH_2$)-O$R^{12}$);" and insert -- =C($R^{11}$)–C($NH_2$)-O$R^{12}$; --, therefor.

In Claim 1, Column 51, Line 58, delete "N,N-di-$C_1C_6$-alkylaminocarbonyl," and insert -- N,N-di-$C_1$-$C_6$-alkylaminocarbonyl, --, therefor.

In Claim 1, Column 51, Line 59, delete "N,N," and insert -- N,N- --, therefor.

In Claim 1, Column 52, Lines 6-7, delete "N,N-di-$C_1C_6$-alkylaminocarbonyl," and insert -- N,N-di-$C_1$-$C_6$-alkylaminocarbonyl, --, therefor.

In Claim 1, Column 52, Line 8, delete "N,N," and insert -- N,N- --, therefor.

In Claim 1, Column 52, Line 20, delete "$C_1$-$C_1$-" and insert -- $C_1$-$C_4$- --, therefor.

In Claim 1, Column 52, Lines 32-33, delete "N,N-di-$C_1C_6$-alkylaminocarbonyl," and insert -- N,N-di-$C_1$-$C_6$-alkylaminocarbonyl, --, therefor.

Signed and Sealed this
Eighteenth Day of April, 2017

Michelle K. Lee
*Director of the United States Patent and Trademark Office*

In Claim 1, Column 52, Line 33, delete "N,N," and insert -- N,N- --, therefor

In Claim 1, Column 52, Line 35, delete "H" insert -- H, --, therefor.